(12) United States Patent
Mash et al.

(10) Patent No.: US 9,783,535 B2
(45) Date of Patent: *Oct. 10, 2017

(54) SUBSTITUTED NORIBOGAINE

(71) Applicant: DemeRx, Inc., Fort Lauderdale, FL (US)

(72) Inventors: Deborah C. Mash, Miami, FL (US);
Richard D. Gless, Oakland, CA (US);
Robert M. Moriarty, Michiana Shores, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/654,503

(22) PCT Filed: Dec. 20, 2012

(86) PCT No.: PCT/US2012/071052
§ 371 (c)(1),
(2) Date: Jun. 19, 2015

(87) PCT Pub. No.: WO2014/098877
PCT Pub. Date: Jun. 26, 2014

(65) Prior Publication Data
US 2015/0329536 A1    Nov. 19, 2015

(51) Int. Cl.
*A61K 31/55* (2006.01)
*C07D 453/06* (2006.01)
*A61K 45/06* (2006.01)
*A61K 31/485* (2006.01)
*C07D 471/22* (2006.01)

(52) U.S. Cl.
CPC .......... *C07D 453/06* (2013.01); *A61K 31/485* (2013.01); *A61K 31/55* (2013.01); *A61K 45/06* (2013.01); *C07D 471/22* (2013.01)

(58) Field of Classification Search
CPC .............................. A61K 31/55; C07D 453/06
USPC ..................................... 514/214.02; 540/579
See application file for complete search history.

(56) References Cited

U.S. PATENT DOCUMENTS

| 2,813,873 A | 11/1957 | Janot et al. |
| 2,877,229 A | 3/1959 | Taylor |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et al. |
| 3,716,528 A | 2/1973 | Nagata et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,422,955 A | 12/1983 | Bryant |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,737,586 A | 4/1988 | Potier et al. |
| 4,806,341 A | 2/1989 | Chien et al. |
| 4,857,523 A | 8/1989 | Lotsof |
| 4,904,768 A | 2/1990 | Saulnier et al. |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,616,575 A | 4/1997 | Efange et al. |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |

(Continued)

FOREIGN PATENT DOCUMENTS

| CA | 2039197 | 9/1995 |
| CN | 1915993 A | 2/2007 |

(Continued)

OTHER PUBLICATIONS

Communication issued on EP 11743404.3, mailed Nov. 16, 2015.
Notification of Defects in Application issued on Israeli Application 232724, mailed Nov. 4, 2015.
Office Action issued on Russian Application 2013139382, mailed Dec. 4, 2015, English translation provided.
Vutukuri et al., "A Mild Deprotection Strategy for Allyl-Protecting Groups and Its Implications in Sequence Specific Dendrimer Synthesis," J.Org. Chem, vol. 68, 2003, pp. 1146-1149.
Examination Report issued on Australian Application 2012209332, mailed Feb. 10, 2016.
Office Action issued on Chinese Application 201180038173.7, mailed Jan. 8, 2016, English translation provided.
Office Action on Chinese Application 201110083808.7, mailed Jul. 15, 2015 English translation provided.
Russian Office Action on Application 2013102923/15 dated May 8, 2015, English translation included.

(Continued)

*Primary Examiner* — Brenda Coleman
(74) *Attorney, Agent, or Firm* — Foley & Lardner LLP

(57) ABSTRACT

This invention relates noribogaine derivatives, compositions and methods of use thereof.

23 Claims, No Drawings

(56) References Cited

U.S. PATENT DOCUMENTS

| | | | |
|---|---|---|---|
| 6,291,675 B1 | 9/2001 | Coop et al. | |
| 6,348,456 B1 | 2/2002 | Mash et al. | |
| 6,451,806 B2 | 9/2002 | Farrar | |
| 6,806,291 B1 | 10/2004 | Sunkel et al. | |
| 6,864,271 B2 | 3/2005 | Bazan et al. | |
| 7,220,737 B1 | 5/2007 | Mash | |
| 7,737,169 B2 | 6/2010 | Corrie et al. | |
| 7,745,479 B2 | 6/2010 | Nettekoven et al. | |
| 7,754,710 B2 | 7/2010 | Mash | |
| 8,017,151 B2 | 9/2011 | Batrakova et al. | |
| 8,178,524 B2 | 5/2012 | Mash | |
| 8,362,007 B1 | 1/2013 | Mash et al. | |
| 8,637,648 B1 | 1/2014 | Mash et al. | |
| 8,741,891 B1* | 6/2014 | Mash | C07D 471/22 514/214.02 |
| 8,765,737 B1 | 7/2014 | Mash et al. | |
| 8,802,832 B2 | 8/2014 | Mash et al. | |
| 8,853,201 B2* | 10/2014 | Gless, Jr. | C07D 471/18 514/214.02 |
| 8,940,728 B2* | 1/2015 | Mash | C07D 471/22 514/214.02 |
| 9,045,481 B2* | 6/2015 | Mash | C07D 471/22 |
| 9,051,343 B2* | 6/2015 | Gless, Jr. | C07F 9/6561 |
| 2003/0153552 A1 | 8/2003 | Mash et al. | |
| 2003/0158202 A1 | 8/2003 | Caldirola et al. | |
| 2006/0051317 A1 | 3/2006 | Batrakova et al. | |
| 2007/0185085 A1 | 8/2007 | Mash | |
| 2009/0264653 A1 | 10/2009 | Bartolini et al. | |
| 2010/0249105 A1 | 9/2010 | Schrimpf et al. | |
| 2010/0311722 A1 | 12/2010 | Mash | |
| 2010/0311723 A1 | 12/2010 | Mash | |
| 2010/0311724 A1 | 12/2010 | Mash | |
| 2010/0311725 A1 | 12/2010 | Mash | |
| 2012/0083485 A1 | 4/2012 | Mash | |
| 2012/0253037 A1 | 10/2012 | Moriarty et al. | |
| 2013/0072472 A1 | 3/2013 | Gless et al. | |
| 2013/0131046 A1 | 5/2013 | Moriarty et al. | |
| 2013/0165414 A1 | 6/2013 | Gless et al. | |
| 2013/0165647 A1 | 6/2013 | Moriarty et al. | |
| 2013/0303756 A1 | 11/2013 | Mash et al. | |
| 2014/0179684 A1 | 6/2014 | Mash et al. | |
| 2014/0179685 A1 | 6/2014 | Mash et al. | |
| 2014/0315837 A1 | 10/2014 | Mash et al. | |
| 2014/0315891 A1 | 10/2014 | Mash | |
| 2014/0357741 A1 | 12/2014 | Mash et al. | |
| 2015/0238503 A1* | 8/2015 | Maillet | A61K 31/55 514/214.02 |
| 2015/0258104 A1* | 9/2015 | Friedhoff | A61K 31/55 514/214.02 |
| 2015/0258105 A1* | 9/2015 | Maillet | A61K 31/55 514/214.02 |
| 2015/0258106 A1* | 9/2015 | Friedhoff | A61K 31/55 514/214.02 |
| 2015/0329536 A1* | 11/2015 | Mash | C07D 471/22 514/210.21 |
| 2015/0361080 A1 | 12/2015 | Mash et al. | |
| 2016/0115185 A1* | 4/2016 | Gless, Jr. | C07F 9/6561 514/80 |

FOREIGN PATENT DOCUMENTS

| | | |
|---|---|---|
| DE | 22 17 132 | 10/1972 |
| EP | 1 491 197 A1 | 12/2004 |
| EP | 2 338 494 | 6/2011 |
| EP | 2 481 740 A1 | 8/2012 |
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 01-100188 | 4/1989 |
| JP | 04-221315 | 8/1992 |
| JP | 2000-501702 | 2/2000 |
| JP | 2001-511776 | 8/2001 |
| JP | 2002-507570 A | 3/2002 |
| JP | 2007-511542 | 5/2007 |
| JP | 2014-503584 A | 2/2014 |
| JP | 2015-500833 | 1/2015 |
| JP | 2015-509075 | 3/2015 |
| JP | 2015-522522 | 8/2015 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |
| WO | WO-97/20847 | 6/1997 |
| WO | WO-98/33802 | 8/1998 |
| WO | WO-99/11250 | 3/1999 |
| WO | WO-99/48501 | 9/1999 |
| WO | WO-2005/049627 | 6/2005 |
| WO | WO-2007/012464 | 2/2007 |
| WO | WO-2007/070892 | 6/2007 |
| WO | WO-2010/036998 | 4/2010 |
| WO | WO-2011/022772 | 3/2011 |
| WO | WO-2012/012764 A1 | 1/2012 |
| WO | WO-2012/103028 | 8/2012 |
| WO | WO-2013/065850 | 5/2013 |
| WO | WO-2013/085849 A2 | 6/2013 |
| WO | WO-2013/085850 | 6/2013 |
| WO | WO-2013/085922 A1 | 6/2013 |
| WO | WO-2013/148572 | 10/2013 |

OTHER PUBLICATIONS

Second Office Action issued on Chinese Application 201280058362.5, mailed Feb. 22, 2016 English translation included.

U.S. Appl. No. 13/566,819, filed Aug. 3, 2012, Mash et al.

U.S. Appl. No. 14/257,841, filed Apr. 21, 2014, Mash, Deborah C.

U.S. Appl. No. 14/298,534, filed Jun. 6, 2014, Mash et al.

U.S. Appl. No. 14/323,743, filed Jul. 3, 2014, Mash et al.

"Analysis—HPLC—Interchim technology", Interchim.com, pp. B31-B93, 1970.

CN Office Action Dated Dec. 3, 2014.

Ahuja, Satinder (Ed.), "Chiral Separation Methods for Pharmaceutical and Biotechnological Products", John Wiley & Sons (published on line Oct. 2010).

Ala-Hurula, et al. "Ergotamine Abuse: Results of Ergotamine Discontinuation, with Special Reference to the Plasma Concentrations," Cephalalgia, 2:4 1982, abstract only.

Ala-Hurula, et al. "Tolfenamic Acid and Ergotamine Abuse," Headache, 21:6, 1981, abstract only.

Alexander. "A Procedure for Drug Screening Without the Need to Transport Urines Use of Ion Exchange Papers and Hem Agglutination Inhibition," Clinical Toxicology, 9:3, 1976, abstract only.

Alim, et al. "Open-Label, Dose Run-Up Study of Diethylpropion in Initial Cocaine Abstinence," Clinical Neuropharmacology, 17:2, 1994, abstract only.

Almeida. "Use and Abuse of Alcohol and Drugs a Clinical Study of Certain Aspects of Their Interrelationship," Boletin de la Oficina Sanitaria Panamericana, 88:1, 1980, abstract only.

Al-Shabanah, et al. "Gastric Antiulcer and Cytoprotective Effects of Cathinone, a Psychoactive Alkaloid of Khat (Catha Edulis Forsk.) and Amphetamine in Rats," Regulatory Peptides, abstract only, 1994.

Altman et al., "An Improved Cu-Based Catalyst System for the Reactions of Alcohols with Aryl Halides," J. Org. Chem., (2008), 73(1):284-286.

Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.

Bagal, et al. "Modulation of Morphine-Induced Antinociception by Ibogaine and Noribogaine," Brain Research, 741:1-2, 1996, pp. 258-262.

Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.

(56) References Cited

OTHER PUBLICATIONS

Batrakova. "Pluronic P85 Enhances the Delivery of Digoxin to the Brain: In Vitro and In Vivo Studies", The Journal of Pharmacology and Experimental Therapy, 296, 2001, pp. 551-557.
Baumann et al. "Comparative Neurobiology of Ibogaine and its Metabolite, 12-Hydroxyibogaimine (Noribogaine), in Rodents." Conference at New York University, Abstract only, 2000.
Baumann et al., In vivo Neurobiological Effects of Ibogaine and Its o-Desmethyl Metabolite, 12 Hydroxyibogamine (Noribogaine), in Rats, J. Pharmacol. Exp. Ther. 2001, vol. 297, No. 2, pp. 531-539.
Beaubrun. "The Diagnosis and Management of Acute Psychotic Reaction Due to Alcohol and Drugs", Caribbean Medical Journal, 36:1, 1975, abstract only.
Beck, et al. "Energy-Dependent Reduced Drug Binding as a Mechanism of Vinca Alkaloid Resistance in Human Leukemic Lymphoblasts", Molecular Pharmacology, 24:3, 1983, abstract only.
Beesley et al., "Chiral Chromatography", John Wiley & Sons (1998).
Benet, et al. "Pharmacokinetics: Biotransformation of Drugs." In Gilman et al. Goodman and Gilman's the Pharmacological Basis of Therapeutics, 1990, pp. 13-16.
Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy , 30:5, 1989, abstract only.
Bert, et al. "Non-Amphetaminic Central Stimulation by Alkaloids from the Ibogaine and Vobasine Series", Planta Medicina, 54:3, 1988, abstract only.
Bhargava, et al. "Effects of ibogaine and noribogaine on the antinociceptive action of mu-, delta- and kappa-opioid receptor agonists in mice", Brain Research 752, 1997, pp. 234-238.
Bloomer et al., "Arc/Arg3.1 Translation Is controlled by Convergent N-Methyl-D-aspartate and Gs-coupled Receptor Signaling Pathways," J. Bio. Chem. (2008), 283(1):582-592.
Blum, et al. "Peyote a Potential Ethnopharmacologic Agent for Alcoholism and Other Drug Dependencies Possible Biochemical Rationale", Clinical Toxicology, 11:4, 1977, abstract only.
Blum, et al. "Possible Role of Tetrahydroisoquinoline Alkaloids in Postalcohol Intoxication States", Annals of the New York Academy of Science, 273, 1976, abstract only.
Blum, et al. "Putative Role of Isoquinoline Alkaloids in Alcoholism: A Link to Opiates", Alcoholism: Clinical and Experimental Research, 2:2, 1978, abstract only.
Brady, et al. "Analgesic Effects of Intraventricular Morphine and Enkephalins in Nondependent and Morphine-Dependent Rats," Journal of Pharmacology and Experimental Therapy, 222:1, 1982, abstract only.
Buchi, et al. "The total synthesis of iboga alkaloids," Jounal of the American Chemical Society, 88, 1966, pp. 3099-3109.
Bundgaard. "Design of Prodrugs: Bioreversible Derivatives for Various Functional Groups and Chemical Entities." Design of Prodrugs, 1-10, 1985.
Bussel, et al. "Isolated Thrombocytopenia in Patients Infected with HIV Treatment with Intravenous Gamma Globulin," American Journal of Hematology, 28:2, 1988, abstract only.
Caccamese et al., "Chiral HPLC Separation and CD Spectra of the Enantiomers of the Alkaloid Tacamonine and Related Compounds", Chirality (2001), 13:691-93.
Caldwell, et al. "The Biochemical Pharmacology of Abused Drugs. III. Cannabis, Opiates, and Synthetic Narcotics," Clinical Pharmacological Therapy, 16:6, 1974, abstract only.
Calpus printout of Watts et al. "Alkaloids from Stemmadenia Species", I. Alkaloids of S. Donnellsmithiii and S. Galleottiana, (1958), vol. 2, pp. 173-182.
Calpus printout of Zetler. "Some Pharmacological Properties of 12 Natural and 11 Partially Synthetic Indole Alkaloids from Tropical Apocyanaceae of the Subtribe Tabernaemontaninae", Arzneimittel-Forschung, (1964), 14:12, pp. 1277-1286.

Cankat. "Pharmacological Aspects of Drug Induced Headache", Functional Neurology, 7:6, 1992, abstract only.
Cappendijk, et al. "The Inhibitory Effect of Norharman on Morphine Withdrawal Syndrome in Rats: Comparison with Ibogaine." Behavioural Brain Research, 65, 1994, pp. 117-119.
Cappendijk, et al. "Inhibitory Effects of Ibogaine on Cocaine Self-Administration in Rats", European Journal of Pharmacology, 241:2-3, 1993, abstract only.
CAS Registry record for "Noribogaine" (1984).
Castle. "Drugs and Fibrotic Reactions—Part I", Adverse Drug React. Bull., 113: abstract only, 1985.
Chaturvedula et al, "New Cytotoxic Indole Alkaloids from Tabernaemontana calcarea from the Madagascar Rainforest", Journal of Natural Products, (2003), vol. 66, pp. 528-531.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny, et al., Opioid responsiveness of cancer pain syndromes caused by neuropathic or nociceptive mechanisms: a combined analysis of controlled, single-dose studies, Neurobiology 44, 1994, pp. 857-861.
Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.
Communication pursuant to Article 94(3) EPC for Appl. No. 11159572.4, dated Apr. 8, 2014.
Communication pursuant to Article 94(3) EPC for Appl. No. 11743404.3, dated Apr. 10, 2014.
Corey, E.J., "Catalytic Enantioselective Diels-Alder Reactions: Methods, Mechanistic Fundamentals, Pathways, and Applications," Angew. Chem. Int. Ed., (2002), 41:1650-1667.
Criel, et al. "Drug Dependent Red Cell Antibodies and Intravascular Haemolysis Occurring in Patients Treated with 9 Hydroxy-Methyl-Ellipticinium," British Journal of Haematology, 46:4, 1980, abstract only.
Damstrup, et al. "Retroperitoneal Fibrosis After Long-Term Daily Use of Ergotamine," International Urology and Nephrology, 18:3, 1986, abstract only.
Database Registry (Online), Chemical Abstracts Service, Columbus Ohis, US Nov. 16, 1984, "ibogamine-18-carboxylic acid, 12-methoxy-,potassium sal," XP002638006, Database accession No. 5500-12-9.
Deecher, et al. "Mechanisms of Action of Ibogaine and Harmaline Congeners Based on Radioligand Binding Studies." Brain Research 571, 1992, pp. 242-247.
Diener, et al. "Analgesic-Induced Chronic Headache Long-Term Results of Withdrawal Therapy," Journal of Neurology, 236:1, 1989, abstract only.
Dierckx, et al. "Intraarterial Sodium Nitroprusside Infusion in the Treatment of Severe Ergotism," Clinical Neuropharmacology, 9:6, 1986, abstract only.
Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.
Eberwine, et al. "Molecular Analysis of Cellular Responses to Opiate Use", Fidia Research Foundation Symposium Series 7 (Neurotransmitter Regulation of Gene Transcription) 1991, abstract only.
Elkind. "Drug Abuse and Headache", Medical Clinics of North America, 75:3, 1991, abstract only.
EP Office Action, Communication Pursuant to Article 94(3) EPC dated Jun. 4, 2013 in related European Patent Application No. 11159572.4.

(56) References Cited

OTHER PUBLICATIONS

European extended search report for EP Appl. No. 12763567.0 dated Oct. 20, 2014.
European Office Action dated Apr. 17, 2015 in European Patent Application No. 11743404.
Evenson. "Developments in Therapeutic Drug Monitoring and Alkaloid Analysis", Federation Proceedings, 34:12, 1975, abstract only.
Extended European Search Report dated Jun. 6, 2011 in related European Patent Appl. No. 11159572.4.
Extended European Search Report issued on 12754746,5, mailed Apr. 23, 2015.
Faglia, et al. "Dihydroergocryptine in Management of Microprolactinomas," Journal of Clinical Endocrinology & Metabolism, 65:4, 1987, abstract only.
Fairchild, et al. "Keynote Address: Multidrug Resistance: A Pleiotropic Response to Cytotoxic Drugs," International Journal of Radiation, Oncology, Biology, & Physics, 20:2, 1991, abstract only.
Finkle. "Phencyclidine Identification by Thin-Layer Chromatography. A Rapid Screening Procedure for Emergency Toxicology", American Journal of Clinical Pathology, 70:2, 1978, abstract only.
First Examination Report for Australian Appl. No. 614366, dated Apr. 11, 2014.
First Office Action for Chinese Appl. No. 201180038173.7, dated Mar. 25, 2014.
Fonne-Pfister, et al. "Xenobiotic and Endobiotic Inhibitors of Cytochrome P-450db1 Function, the Target of the Debrisoquine / Sparteine Type Polymorphism," Biochemical Pharmacology, 37:20, 1988, abstract only.
Frances, et al. "Effects of Ibogaine on Naloxone-Precipitated Withdrawal in Morphine-Dependent Mice", Fundamental Clininical Pharmacology, 6:8-9, 1992, abstract only.
Futatsugi, et al., "Oxazaborolidine-Derived Lewis Acid Assited Lewis Acid as a Moisture-Tolerant Catalyst for Enantioselective Diels-Alder Reactions," Angew. Chem. Int. Ed., (2005), 44:1484-1487.
Gabr, et al. "Changes in Absolute Amount of Alkaloids in Datura-Metel Treated with Certain Growth Regulators", Herba Pol, 21:2, 1975, abstract only.
Garcia, et al. Chronic pain states: pathophysiology and medical therapy, Seminars in Arthritis and Rheumatism, 27, 1997, pp. 1-16.
Gennaro. "Remington: The Science and Practice of Pharmacy", Mack Publishing Col., vol. II, 1995, pp. 1736 & 1814.
George, et al. "Palliative medicine", Postgraduate Medical Journal, vol. 69, 1993, pp. 426-449.
Gifford, A. N. and Johnson, K. Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.
Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994, pp. 14-22.
Glick, et al. "Effect of Ibogaine on Acute Signs of Morphine Withdrawal in Rats: Independence from Tremor", Neuropharmacology, 31:5, 1992, abstract only.
Glick, et al. "Effects of Aftereffects of Ibogaine on Morphine Self-Administration in Rats", European Journal of Pharmacology, 195:3, 1991, abstract only.
Glick, et al. "Ibogaine-like effects of noribogaine in rats", Brain Research, 713, 1996, pp. 294-297.
Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.
Gold, et al. "Effect of Methadone Dosage on Clonidine Detoxification Efficacy", American Journal Psychiatry, 137:3, 1980, abstract only.
Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.
Greenwald, et al., "Poly(ethylene glycol) conjugated drugs and prodrugs: a comprehensive review," Crit. Rev. Ther. Drug Carrier Syst., (2000), 17(2):101-161.
Gross. "Effect of Ergot Alkaloids on Serum Prolactin in Non-Psychotic Organic Brain Syndrome of the Elderly", Experimental Aging Research, 5:4, 1979, abstract only.
Gunn. "Relations Between Chemical Constitution, Pharmacological Actions, and Therapeutic Uses, in the Harmine Group of Alkaloids." From the Pharmacological Laboratory, University of Oxford, 1935, pp. 379-396.
Haber, et al. "Tetrahydroisoquinolines—Endogenous Products After Chronic Alcohol Abuse", Pharmazie, 47:1, 1992, abstract only.
Halikas, et al. "Treatment of Crack Cocaine Use with Carbamazepine", American Journal of Drug and Alcohol Abuse, 18:1, 1992, abstract only.
Hanks. "Opioid-responsive and opioid-non-responsive pain in cancer," British Medical Bulletin 47, 1991, pp. 718-731.
Hardman, et al. "Goodman & Gilman's The Pharmacological Basis of Therapeutics" (9th ed, 1996) p. 51 and pp. 57-58.
Harsing, et al. "Evidence that Ibogaine Releases Dopamine from the Cytoplasmic Pool in Isloated Mouse Striatum", Journal of Neural Transmission General Section, 96:3, 1994, abstract only.
Hearn, et al. "Identification and Quantitation of Ibogaine and an o-Demethylated Metabolite in Brain and Biological Fluids Using Gas Chromatography-Mass Spectrometry." Journal Analytical Toxicology, 19, 1995, pp. 427-434.
Heel, et al. "Buprenorphine: A Review of Its Pharmacological Properties and Therapeutic Efficacy", Drugs, 17:2, 1979, abstract only.
Henry, et al. "Reversible Cerebral Arteriopathy Associated with the Administration of Ergot Derivatives", Cephalalgia, 4:3, 1984, abstract only.
Ho, et al. "Metabolism of Harmaline in Rats." Biochemical Pharmacology vol. 20, 1971, pp. 1313-1319.
Hoes. "Clinical Criteria for the Selection of Anxiolytics", Tijdschrift voor Therapie Geneesmiddel en Onderzoek, 9:9, 1984, abstract only.
Holbrook. "Nicotine Addiction." in Isselbacher et al. (ed.), "Harrison's Principals of Internal Medicine" 13th Ed., McGraw-Hill Inc., 1994, 2433-2437.
Holzner, et al. "The Neuroleptic Sleeping Course in Chronic Headache", Therapiewoche, 35/36: 1985, abstract only.
Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.
Hubens, et al. "Chronic Intake of a Hydrogenated Ergot Alkaloid Causing Peripheral Vascular Ischemia—A Case Report", Journal of Vascular Surgery, 21:4, 1987, abstract only.
Huffman, et al. "A Formal Synthesis of (±)-Ibogamine," Journal of Organic Chemistry, vol. 50, 1985, pp. 1460-1464.
International Preliminary Report on Patentability for PCT/US2012/067799, dated Jun. 19, 2014.
International Preliminary Report on Patentability for PCT/US2012/071052, issued Jun. 23, 2015.
International Search Report and Written Opinion dated Mar. 11, 2013 in related PCT Patent Application No. PCT/US12/71052.
International Search Report and Written Opinion dated Oct. 31, 2012 in related PCT Application No. PCT/US2012/030405.
International Search Report and Written Opinion dated Oct. 4, 2012 in related PCT Application Serial No. PCT/US2012/022255.
International Search Report for PCT/US2011/045081 dated Oct. 4, 2011.
Isler. "Treatment of Headache", Schweizerische Medizinische Wochenschrift, 114:35, 1984, abstract only.
Jaffe. "Drug Addiction and Drug Abuse", Goodman and Gilman's The Pharmacological Basis of Therapeutics, 8th Ed., pp. 520-523 & pp. 559-568, 1990.
Jaffe. "Psychopharmacology and Opiate Dependence," U.S. Public Health Services Publication, 1957-1967: pp. 1836, 1967.

(56) References Cited

OTHER PUBLICATIONS

James. "Linkers for solid phase organic synthesis," Tetrahedron, 55, 1999, pp. 4855-4946.
Jana et al., "Progress in the Synthesis of Iboga-alkaloids and their Congeners," Organic Preparation and Procedures International, (2011), 43:541-573.
Jana et al., "Total synthesis of ibogaine, epiibogaine and their analogues", Tetrahedron. 2012. vol. 68, pp. 7155-7165.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985, abstract only.
Jansen, et al. "Ethnopharmacology of Kratom and the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.
Jarraya, et al., "N-(Hydroxymethyl)ibogaine," Acta Cryst., (2008), E64—vol. 64(9):o1739.
Justins. "Management strategies for chronic pain," Annals of the Rheumatic Diseases, vol. 55, 1996, pp. 588-596.
Kagan, et al., "Catalytic Asymmetric Diels-Alder Reactions," Chem. Rev., (1992), 92:1007-1019.
Kalix. "Khat: A Plant with Amphetamine Effects," Journal of Substance Abuse Treatment, 5:3, 1988, abstract only.
Kalix. "Pharmacological Properties of the Stimulant Khat", Pharmacological Therapy, 48:3, 1990, abstract only.
Keefner. "A Gas Chromatography-Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Kingston et al., "Cytotoxicity of Modified Indole Alkaloids", Journal of Pharmaceutical Sciences, 68:11, Nov. 1979, pp. 1403-1405.
Knoll. "Azidomorphines and Homopyrimidazols: a New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.
Konig. "Psychiatric Intensive Therapy After Acute Alkaloid Withdrawal Syndrome", Infusionsther Klin Ernahr, 6:1, 1979, abstract only.
Kontrimaviciute et al., "Liquid chromatography-electrospray mass spectrometry determination of ibogaine and noribogaine in human plasma and whole blood: Application to a poisoning involving Tabernanthe iboga root" J. Chromatog. B (2006), 843, 131-41.
Kornetsky. "Pharmacology Drugs Affecting Behavior." John Wiley & Sons, 1976, pp. 185-187.
Kostowski, et al. "The Effects of Some Hallucinogens on Aggressiveness of Mice and Rats" Pharmacology, 7, 1972, pp. 259-263.
Krug. "Cocaine Abuse: Historical, Epidemiologic, and Clinical Perspectives for Pediatricians", Advances in Pediatrics, 36:369-406, 1989.
Kuehne et al., "Biomimetric syntheses of indole alkaloids. 11. Syntheses of .beta.-carboline and indoloazepine intermediates," J. Org. Chem., (1985), 50(7):919-924.
Kupers, et al. "Morphine differentially affects the sensory and affective pain ratings in neuorgenic and idiopathic forms of pain." Pain, 47, 1991, pp. 5-12.
Kuroch et al., "Voacanga Africana: Chemistry, Quality and Pharmacological Activity" ACS Symposium Series 1021 (African Natural Plant Products), (2009), 363-80.

Lakoski, et al. "Electrophysiologic Characterization of an Ibogaine Metabolite in Dorsal Raphe Nucleus and Hippocampus." Society for Neuroscience, 21:716, 1995, abstract only.
Larson-Prior, et al. "Electrophysiologic Characterization of an Ibogaine Metabolite in the Cerebellar Cortex." Society for Neuroscience, 21:716, 1995, abstract only.
Layer, et al., "Structurally modified ibogaine analogs exhibit differing affinities for NMDA receptors," European Journal of Pharmacology, 1996, 309:159-165.
Lemontt, et al. "Increase MDR Gene Expression and Decreased Drug Accumulation in Multidrug-Resistant Human Melanoma Cells", Cancer Research, 48:22, 1988, abstract only.
Leonard, J. "A Practical Introduction to Separation and Purification techniques for the Beginning Organic Chemistry Laboratory", Chem. Ed. (1981), 58, 1022-23.
Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.
Lerida, et al. "Incidence of Morphine Withdrawal and Quasi-Abstinence Syndrome in a Model of Chronic Pain in the Rat," Neuroscience, 81:1-2, 1987, abstract only.
Lewis, "Studies on the synthesis and biosynthesis of indole alkaloids", The Faculty of Graduate Studies Department of Chemistry University of British Columbia, (1978), See compound 220, Figure 57. abstract only.
Lewis, et al. "Adverse Reactions and Interactions with .beta.-Adrenoceptor Blocking Drugs," Journal of Medical Toxicology, 1:5, 1986, abstract only.
Lewis, et al. "Narcotic Analgesics and Antagonists," Annual Review of Pharmacology, 11, 1971, abstract only.
Licht, et al. "Induction of Multiple-Drug Resistance During Anti-Neoplastic Chemotherapy In-Vitro," International Journal of Cancer, 49:4, 1991, abstract only.
Ling, et al. "Drugs of Abuse-Opiates", in Addtiction Medicine [Special Issue], Western Journal of Medicine, 152, 1990, pp. 565-572.
Low, et al. "Effects of Acronycine and Cytouchalasin B on the Division of Rat Leukemia Cells," Experimental Cell Research, 131:1, 1981, abstract only.
Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.
Maisonneuve, et al. "Interactions of Ibogaine and D-Amphetamine: in vivio Microdialysis and Motor Behavior in Rats." Brain Research 579, 1992, pp. 87-92.
Maisonneuve, et al. "Acute and Prolonged Effects of Ibogaine on Brain Dopamine Metabolism and Morphine-Induced Locomotor Activity in Rats", Brain Research, 575:1, 1992, abstract only.
Maisonneuve, et al. "Interactions Between Ibogaine, a Potential Anti-Addictive Agent, and Morphine: an in Vivo Microdialysis Study," European Journal of Pharmacology, 199:1, 1991, abstract only.
Martellotta, et al. "Effects of the Calcium Antagonist Isradipine on Cocaine Intravenous Self-Administration in Rats", Psychopharmacologia, 113:3-4, 1994, abstract only.
Martin, et al. "Neuropathic Pain in Cancer Patients: Mechanisms, Syndromes, and Clinical Controversies," Journal of Pain and Symptom Management, 14:2, 1997, pp. 99-117.
Mash, et al. "Ibogaine in the Treatment of Heroin Withdrawal," The Alkaloids 56, 2001, pp. 1-17.
Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995, abstract only.
Mash, et al. "Preclinical screening of an ibogaie metabolite (noribogaine) on cocaine-induced hyperlocomotion and cocaine self-administration." Society of Neurosciences, vol. 22, 1996, abstract only.
Mash, et al. "Properties of Ibogaine and its Principle Metabolite (12-hydroxyibogamine) at the MK-801 binding site of the NMDA receptor complex," Neuroscience Letters, 192, 1995, pp. 53-56.

(56) References Cited

OTHER PUBLICATIONS

Mateer, et al. "Reversible Ipecac Myopathy," Archives of Neurology, 42:2, 1985, abstract only.
Matharu, et al. "Preformulation and Development of Ibogaine Injection for the Treatment of Drug Abuse," Pharmaceutical Research, 10: 1993, abstract only.
Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.
Mcneish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.
Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.
Mendelson & Mello "Cocaine and Other Commonly Abused Drugs." In Isselbacher et al. (ed.), "Harrison's Principals of Internal Medicine." 13th Ed., McGraw-Hill Inc., 1994, pp. 2429-2433.
Menzies, et al. "Gangrene of the Small Bowel: A Complication of Methysergide Therapy," Australian and New Zealand Journal of Surgery, 52:5, 1982, abstract only.
Metelitsa. "Pharmacological Agents in Controlling Smoking," Biull Vsesoiuznogo Kardiol Nauchn Tsentra, 10:1, 1987, abstract only.
Millan. "k-Opioid Receptors and Analgesia," Trendes in Pharmacologicla Sciences, 11, 1990, pp. 70-76.
Mizuhashi, et al. "Antitumor Activities of IKP-104 A 4-1H Pyridizinone Derivative on Cultured and Implanted Tumors," Japanese Journal of Cancer Research, 81:12, 1990, abstract only.
Montefiori, et al. "In Vitro Evaluation of Mismatched Double-Stranded RNA (Ampligen) for Combination Therapy in the Treatment of Acquired Immunodeficiency Syndrome," AIDS Research and Human Retroviruses, 5:2, 1989, abstract only.
Mulamba, et al. "Alkaloids from Tabernathe Pubescens," Journal of Natural Products, vol. 44:2, 1981, pp. 184-189.
Naikwadi et al., "Liquid Chromatography of Phenolic Compounds on a Microbore Anion Exchange Resin Column," Analytical Chemistry, 56:8, 1984, p. 1525-1527.
Naranjo. "Ibogaine in psychotherapy: psychoanalysis according to Naranjo", part IV, pp. 1-2. http://www.nettuno.it/fiera/electric.italy/bwitif:html (1969).
Niemann et al, "The Isolation of Rupicoline and Montanine, Two Pseudoindoxyl Alkaloids of Tabernaemontana Rupicola Benth", The Journal of Organic Chemistry, 31(7):2265-2269, 1966.
Nishiyama, et al. "Expression of the Multidrug Transporter, P-Glycoproteiin, in Renal and Transitional Cell Carcinomas," Cancer, 71:11, 1993, pp. 3611-3619.
Nooter, et al. "Multidrug Resistance (MDR) Genes in Haematological Malignancies," Cytotechnology, 12:1-3, 1993, abstract only.
Nunn-Thompson, et al. "Pharmacotherapy for Making Cessation", Clin Pharm, 8:10, 1989, abstract only.
Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.
Office Action for Israeli Patent Application No. 227593 dated Nov. 13, 2013.
Office Action on Chinese Application 201280058362.5, issued Aug. 5, 2015, English translation provided.
Office Action on Japanese Application 2013-520892, mailed Jul. 7, 2015.
O'Hearn, et al. "Degenration of Prukinje Cells in Parasagittal Zones of the Cerebellar Vermis After Treatment with Ibogaine of Harmaline," Neuroscience, 55:2, 1993, abstract only.
O'Hearn, et al. "Ibogaine Induces Glial Activation in Parasagittal Zones of the Cerebellum," Neuroreport, 4:3, 1993, abstract only.
Pablo, et al, "Noribogaine Stimulates Naloxone-Sensitive[35S]GTPgammaS Binding," NeuroReport, 9, 1998, pp. 109-114. (Website Publication Date of Dec. 20, 1997.).

Pacifici, et al. "Immunological Effect of Cocaine and Host Resistance in Mice," International Journal of Immunotherapy, 8:2, 1992, abstract only.
Palyi. "Survivial Responses to New Cytostatic Hexitols of P388 Mouse and K562 Leukemia Cells in Vitro," Cancer Treatment Reports, 70:2, 1986, abstract only.
Pantazis, et al. "Efficacy of Camptothecin Congeners in the Treatment of Human Breast Carcinoma Xenografts," Oncology Research, 5:8, 1994, abstract only.
PCT International Preliminary Report on Patentability dated Jul. 30, 2013 in related PCT International Patent Application No. PCT/US2012/022255.
PCT International Search Report and Written Opinion dated Dec. 8, 2014 for PCT Application No. PCT/US2014/031364.
PCT International Search Report and Written Opinion dated Jan. 21, 2015 in PCT Patent Application No. PCT/US2014/034826.
PCT International Search Report and Written Opinion for related PCT/US2013/022874, dated Jun. 28, 2013.
PCT International Search Report and Written Opinion in related PCT Patent Application No. PCT/US12/67799, dated Mar. 28, 2013.
PCT International Search Report in PCT/US2012/067629 dated Mar. 13, 2013.
Pehek. "Effects of Cathinone and Amphetamine on the Neurochemistry of Dopamine in Vivo," Neuropharmacology, 29:12, 1990, abstract only.
Percheron et al., Ibogaine et vocangine. Compt. Rend. Acad. Sci., (1957), 245:1141-1143.
Perera, et al. "Tertiary Indole Alkaloids of Tabernaemontana Dichotoma Seeds," Planta Medica, 49:1, 1983, abstract only.
Perrin. "Clinical Pharmacokinetics of Ergotamine in Migraine and Cluster Headache," Clinical Pharmacokinetics, 10:4, 1985, abstract only.
Popik, et al. "NMDA Antagonist Properties of the pUtative Antiaddictive Drug, Ibogaine," Journal of Pharmaceutical and Experimental Therapeutics, 275:2, 1995, pp. 753-760.
Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.
Popik, et al. "100 Years of Ibogaine: Neurochemical and Pharmacological Actions of a Putative anti-addictive Drug," Pharmacological Reviews 47:2, 1995, pp. 235-253.
Pulvirenti, et al. "Lisuride Reduces Intravenous Cocaine Self-Administration in Rats," Pharmacology, Biochemistry and Behavior, 47:4, 1994, abstract only.
Qiu, et al. "The Influence of Chronic Nicotine Treatment on Stress-Induces Gastric Ulceration and Emptying Rate in Rats," Experientia, 48:4, 1992, abstract only.
Radouco-Thomas, et al. "Adverse effects to Psychotomimetics. Proposition of a Psychopharmacological Classification." Pharmacologie, Toxicologie, et abus des psychotomimetiques (hallucinogens), (1974), 109, abstract only.
Rezvani, et al. "Noribogaine, a Primary Ibogaine Metabolite, Reduces Alcohol Intake in P and Fawn-Hooded Rats." RSA Annual Scientific Meeting, 1995, abstract only.
Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.
Ricceri, et al. "Postnatal cocaine Esposure Affects Neonatal Passive Avoidance Performance and Cholinergic Development in Rats," Pharmacology, Biochemistry and Behavior, 45:2, 1993, abstract only.
Rodriguez, et al. "Cocaine Adminstration Prior to Reactivation Facilitates Later Acquisition of an Avoidance Response in Rats," Psychopharmacologia, 112:2-3, 1993, abstract only.
Rosenmund, et al. "Ibogamin, Ibogain and Epiibogamin" Chemische Berichte, 108, 1975, pp. 1871-1895.
Sachs, et al. "Corneal Complications Associated with the Use of Crack Cocaine," Ophthalmology, 100:2, 1993, abstract only.
Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.

(56) References Cited

OTHER PUBLICATIONS

Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2, 1989, abstract only.
Saper, et al. "Ergotamine Tartrate Dependency: Features and Possible Mechanisms," Clinical Neuropharmacology, 9:3, 1986, abstract only.
Schecter, et al. "Comparison of the Behavioral Effects of Ibogaine from Three Sources: Mediation of Discriminative Activity," European Journal of Pharmacology, 249:1, 1993, abstract only.
Schneider, et al. "Analysis of the Cardiovascular Action of Ibogaine Hydrochloride." Archives Internationales de Pharmacodynamie et de Thérapie, 110, 1957, pp. 92-102.
Schneider, et al. "Neuropharmacological Studies of Ibogaine: An Indole Alkaloid with Central Stimulant Properties." Annals of the New York Academy of Sciences, 66, 1957, pp. 765-776.
Schneider, et al., "Potentiation Action of Ibogaine on Morphine Analgesia" Experiential, 12, 1956, pp. 323-324.
Schnider, et al. "Use and Abuse of Analgesics in Tension-Type Headache," Cephalalgia, 14:2, 1994, abstract only.
Schuckit & Segal. "Opiod Drug Use." in Isselbacher et al. (ed.), "Harrison's Principals of Internal Medicine" 13th Ed., McGraw-Hill Inc., 1994, 2425-2429.
Schuckit. "Alcohol and Alcoholism," In Isselbacher et al. (ed.), "Harrison's Principals of Internal Medicine." 13th Ed., McGraw-Hill Inc., 1994, pp. 2420-2425.
Seeber, et al. "In Vivo Resistance Towards Anthracyclines, Etoposide, and Cis-Diamminedichloroplatinum (II)," Cancer Research, 42:11, 1982, abstract only.
Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988, abstract only.
Sershen, et al. "Ibogaine Antagonizes Cocaine-Induced Locomotor Stimulation in Mice," Life Sciences, 50:15, 1992, abstract only.
Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.
Sershen, et al. "Ibogaine Reduces Preference for Cocaine Consumption in C57BL/6By Mice," Pharmacology Biochemistry and Behavior, 47:1, 1994, abstract only.
Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.
Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula, et al. "Rationale for Design for Biologically Reversible Drug Derivatives: Prodrugs." Journal of Pharmaceutical Sciences, 64:2, 1975, pp. 181-210.
Sjostromt et al., "Ion Exchange Separation Method for Microdetermination of Tropane Alkaloids in the Presence of Mkphine," 1959, XP55182014.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats." The Journal of Pharmacology and Experimental Therapeutics, 173:1, 1970, pp. 26-30.
Slotkin, et al. "Urinary Metabolites of Harmine in the Rat and their Inhibition of Monoamine Oxidase." Biochemical Pharmacology, 19, 1970, pp. 125-131.

Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Snyder, et al., "Practical HPLC Method Development", 1997, 2nd Ed., pp. 214-218, 266, 267, 282 & 283, John Wiley & Sons, Inc.
Solinas, et al. "Solid-Supported Reagents and Catch-and-Release Techniques in Organic Synthesis", Synthesis 2007:16, 2007, pp. 2409-2453.
Stahl, et al., "Handbook of Pharmaceutical Salts", 1998, p. 250 John Wiley & Sons.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Stevenson et al, (Ed.), "Chiral Separations", Plenum Press (1987).
Still, et al., "Rapid Chromatorgraphic Technique for Preparative Separations with Moderate Resolutions", J. Org. Chem., (1978), 43, 2923-25.
Sugiyama, et al. "Quantitative Analysis of Cell-Kill Effects of Anticancer Drugs: Consideration of Both In Vitro and In Vivo Expreimental Systems." Gan To Kagaku Ryoho, 14:12, 1987, abstract only.
Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus," J. Pharmacol. Exp. Ther., (2002), 302(1):249-256.
Tarnower, et al., "Ergotism Masquerading as Arteritis," Postgradate Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.
Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Third Office Action on Chinese Application 201180038173.7, issued Jun. 17, 2015—English translation provided.
Toda, Fumio (Ed.), "Enantiomer Separation: Fundamentals and Practical Methods", Kluwer Academic Publishers (2004).
Torrenegra, et al. "Alkaloids of stemmadenia grandiflora", Phytochemistry, 27:6, 1988, pp. 1843-1848.
Toyo'oka, "Resolution of chiral drugs by liquid chromatography based upon diastereomer formation with chiral derivatization reagents", J. Biochem. Biophys. Methods 54, 25-56 (2002).
Trost, et al., "A Total Synthesis of Racemic and Optically Active Ibogamine. Utilization and Mechanism of a New Silver Ion Assisted Palladium Catalyzed Cyclization," J. Am. Chem. Soc., (1978), 100(12):3930-3931.
Trost, et al., "Stereocontrolled Approach to 1,4-Disubstitued 1,3-Dienes," J. Org. Chem., (1978), 43(24):4559-4564.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.

(56) References Cited

OTHER PUBLICATIONS

Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001, pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.
Yang, et al., "Prodrug based optimal drug delivery via membrane transporter/receptor," Expert. Opin. Biol. Ther., (2001), 1(2):159-175.
Zetler, et al. "Pharmacokinetics in the Rat of the Hallucinogenic Alkaloids Harmine and Harmaline." Naunyn-Schmiedeberg's Archives of Pharmacology, 285, 1974, pp. 273-292.
Zetler, et al. "Cerebral Pharmacokinetics of Tremor-Producing Harmala and Iboga Alkaloids" Pharmacology, 7:4, 1972, pp. 237-248.
Buchi et al., "Chemical Transformations of Ibogaine," Journal of the American Chemical Society, 88:11, Jun. 5, 1966, pp. 2532-2535.
Extended European Search Report on EP Application 13740942.1, mailed Sep. 10, 2015.
Glick SD et al., Development of novel medications for drugs addiction. The legacy of an African shrub. AnnN.Y.Acad.Sci. 2000; 909:808-103 abstract[on-line] [found on Aug. 21, 2015]www.ncbi.nlm.nih.gov/pubmed/10911925.
International Search Report & Written Opinion for PCT/US2014/013063 dated Oct. 8, 2015.
JD Roberts, "Separation and Purification. Identification of Organic Compounds by Spectroscopic Techniques," Chapter 9, 1977 pp. 257-349.
Office Action on Russian Application 2013102923/15 dated Aug. 11, 2015 English translation provided.
Peterson, A. L. et al., Treatment of Parkinson's disease with trophic factors. Neurotherapeutics, 2008, vol. 5, No. 2, pp. 270-280.
RN:5500-12-9,Registry (STN) [online] , Nov. 16, 1984.
RN:766444-34-2,Registry (STN) [online], Oct. 20, 2004.
Wang et al., Targeted Delivery of GDNF through the Blood-Brain Barrier by MRI-Guided Focused Ultrasound, PLoS One, vol. 7, Issue 7, Article e52925, internal pp. 1-8, Dec. 2012.
Bandarage et al., Total Syntheses of Racemic Albifloranine and Its Anti-Addictive Congeners, Including 18-Methoxycoronaridine, Tetrahedron, vol. 55, No. 31, pp. 9405-9424 (1999).
CAS Printout of Passarella et al., Nature-Inspired Indolyl-2-Azabicyclo[2.2.2]oct-7-ene Derivatives as Promising Agents for the Attenuation of Withdrawal Symptoms:Synthesis of 20-Desethyl-20-Hydroxymethyl-11-Demethoxyibogaine, Natural Product Research, vol. 20, No. 8, pp. 758-765 (2006).
Huffman et al., The Synthesis of Desethylibogamine, Journal of the American Chemical Society, vol. 87, No. 10, p. 2288 (1965).
International Preliminary Report on Patentability for related application No. PCT/US2014/013063, dated Aug. 4, 2016.
Popik, Piotr, "Facilitation of Memory Retrieval by the 'Anti-Addictive' Alkaloid, Ibogaine", Life Sciences, vol. 59, No. 24, Jan. 1, 1996, pp. 379-385.
Xuan et al., "Antiaddictive indole alkaloids in Ervatamia yunnanensis and their bioactivity", Database CA, Database accession No. 2007:148527, 2006, 27(1), pp. 92-96. (Abstract Only).
Madinaveitia, et al., "A New Rearrangement in Iboga Alkaloids", Helvetica Chimica Acta, vol. 82, pp. 170-176, 1999.

\* cited by examiner

SUBSTITUTED NORIBOGAINE

CROSS-REFERENCE TO RELATED APPLICATIONS

This application is a U.S. National Phase application under 35 U.S.C. §371 of International Patent Application No. PCT/US2012/071052, filed on Dec. 20, 2012, the entirety of which is incorporated by reference herein.

FIELD OF THE INVENTION

This invention relates noribogaine derivatives, compositions and methods of use thereof.

STATE OF THE ART

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tryptamine, tetrahydrohavaine and indolazepines. Noribogaine can be depicted by the following formula:

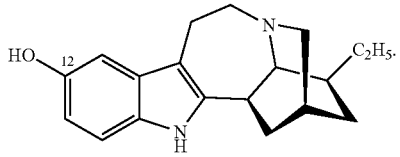

Noribogaine and its pharmaceutically acceptable salts have recently received significant attention as a non-addictive alkaloid useful in treating addiction (U.S. Pat. No. 6,348,456) and as a potent analgesic (U.S. Pat. No. 7,220,737).

Noribogaine has been found to have properties suitable for the treatment of pain and to the withdrawal symptoms associated with drug dependency or abuse. In particular, it is believed that noribogaine binds to two classes of opioid receptors that have been associated with pain relief, the μ and κ receptors. In the case of the p-type receptors, it appears that noribogaine acts as an opiate agonist. In addition, noribogaine elevates brain serotonin levels by blocking synaptic reuptake. It is believed that such levels (as well as ligand interactions at the μ and κ opiate receptors) play a role in the anxiety and drug cravings experienced by addicts during withdrawal.

Noribogaine analogs are also found to inhibit a3b4 nicotinic acetylcholine receptors (nAChRs).

Noribogaine analogs are also found effective for treatment of nicotine addiction and for treatment of other substance abuse related disorders (SRDs).

SUMMARY OF THE INVENTION

This invention relates to noribogaine derivative compounds. Such compounds are contemplated as being useful in treating drug addiction and/or pain. Accordingly, in one of its compound aspects, this invention is directed to a compound or a pharmaceutically acceptable salt thereof wherein said compound is represented by Formula IA or Formula IB, or a pharmaceutically acceptable salt of each thereof:

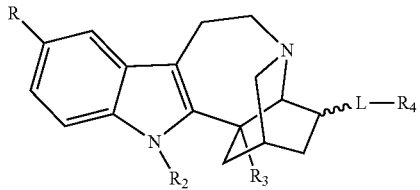

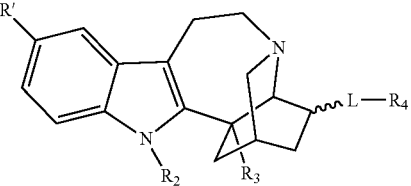

wherein
$R$ is $OR^1$ or $C_1$-$C_{12}$ alkyl optionally substituted with 1 to 5 $R^9$;
$R^1$ is selected from the group consisting of hydrogen, —C(O)OX, —SO$_2$OR$^{10}$, a monophosphate, a diphosphate, a triphosphate, and —C(O)N(Y)$_2$ where X is $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$ heteroaryl having 1 to 4 heteroatoms and which is optionally substituted with 1 to 5 $R^9$, $C_1$-$C_{10}$ heterocyclic having 1 to 4 heteroatoms and which is optionally substituted with 1 to 5 $R^9$, or where each Y, together with the nitrogen atom bound thereto form either a $C_1$-$C_6$ heterocyclic having 1 to 4 heteroatoms and which is optionally substituted with 1 to 5 $R^9$, or a $C_1$-$C_6$ heteroaryl having 1 to 4 heteroatoms and which is optionally substituted with 1 to 5 $R^9$;
R' is halo, $OR^{20}$, or $C_1$-$C_{12}$ alkyl optionally substituted with 1 to 5 $R^9$;
$R^{20}$ is selected from the group consisting of hydrogen, —C(O)X, —C(O)OX and —C(O)N(Y)$_2$ where X and Y are defined as above;
$R^2$ is hydrogen, —SO$_2$OR$^{10}$, a monophosphate, a diphosphate, or a triphosphate;
$R^3$ is selected from the group consisting of hydrogen, —(CH$_2$)$_m$OR$^7$, —CR$^6$(OH)R$^7$, —(CH$_2$)$_m$CN, —(CH$_2$)$_m$COR$^7$, —(CH$_2$)$_m$CO$_2$R$^7$, —(CH$_2$)$_m$C(O)NR$^6$R$^7$, —(CH$_2$)$_m$ C(O)NR$^6$NR$^7$R$^7$, —(CH$_2$)$_m$C(O)NR$^6$NR$^7$C(O)R$^8$, and —(CH$_2$)$_m$NR$^6$R$^7$;
m is 0, 1, or 2;
L is a bond or $C_1$-$C_{12}$ alkylene;
$R^4$ is selected from the group consisting of $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)$_n$—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;
$X^2$ is selected from the group consisting of O and S;
$Y^2$ is $C_1$-$C_4$ alkylene or $C_6$-$C_{10}$ arylene, or a combination thereof;
n is 1, 2, or 3;
$R^6$ and $R^7$ are each independently selected from the group consisting of hydrogen, $C_1$-$C_{12}$ alkyl optionally substituted with 1 to 5 $R^9$, $C_1$-$C_6$ heterocycle having 1 to 4 heteroatoms which is optionally substituted with 1 to 5 $R^9$, $C_3$-$C_{10}$ cycloalkyl optionally substituted with 1 to 5

$R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$; or $R^6$ and $R^7$ are joined to form $C_1$-$C_6$ heterocycle having 1 to 4 heteroatoms which is optionally substituted with 1 to 5 $R^9$;

$R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^9$ is selected from the group consisting of $C_1$-$C_4$ alkyl, phenyl, halo, —OH, —$OR^{10}$, —CN, —$COR^{10}$, —$CO_2R^{10}$, —$C(O)NHR^{10}$, —$NR^{10}R^{10}$, —$C(O)NR^{10}R^{10}$, —$C(O)NHNHR^{10}$, —$C(O)NR^{10}NHR^{10}$, —$C(O)NR^{10}NR^{10}R^{10}$, —$C(O)NR^{10}R^{10}$, —$C(O)NHNHR^{10}$, —$C(O)NHNHC(O)R^{10}$, —$SO_2NR^{10}R^{10}$, —$C(O)NR^{10}NR^{10}C(O)R^{10}$, —$NHC(O)R^{10}$, $C_1$-$C_6$ heterocycle having 1 to 4 heteroatoms optionally substituted with 1 to 5 $R^{10}$, and —$C(O)NR^{10}NHC(O)R^{10}$; and $R^{10}$ is $C_1$-$C_2$ alkyl;

provided that:
for the compound of Formula IA, when R is —OH or $C_1$-$C_{12}$ alkyl optionally substituted with 1 to 5 $R^9$, then $R^3$ is hydrogen; and
for the compound of Formula IA, when $R^3$ is hydrogen, and -L-$R^4$ is ethyl, then R is not —$OR^1$.

This invention is also directed to pharmaceutical compositions comprising a pharmaceutically acceptable excipient and a therapeutically effective amount of a compound of this invention or a mixture of one or more of such compounds.

This invention is still further directed to methods for treating pain and/or addiction in a patient in need thereof, which methods comprise administering to the patient a one or more of compounds or a pharmaceutical composition of this invention.

This invention is also directed to methods of inhibiting a3b4 nicotinic acetylcholine receptors.

This invention is also directed to methods for treating of nicotine addiction and methods for treating of other substance abuse related disorders (SRDs).

DETAILED DESCRIPTION OF THE INVENTION

This invention is directed to ribose substituted noribogaine for use in treating pain and/or addition. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of pharmaceutically acceptable excipients.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

Noribogaine can be depicted by the following Formula:

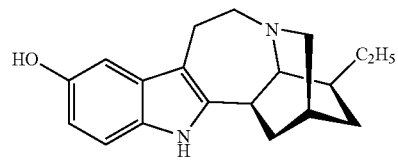

and can be synthesized by the O-demethylation of ibogaine. This may be accomplished, for example, by reacting ibogaine with boron tribromide/methylene chloride at room temperature and then purifying the product using known procedures. Ibogaine may be obtained from natural or commercial sources, or can be synthesized by methods known in the art (see Huffman, et al., J. Org. Chem. 50:1460 (1985)). In addition, noribogaine may also be obtained from the National Institute on Drug Abuse (Rockville, Md.).

As used herein, the term "hydrolyzable group" refers to a group that can be hydrolyzed to release the free hydroxy group under hydrolysis conditions. Examples of hydrolysable group include, but are not limited to those defined for $R^1$ above. Preferred hydrolysable groups include carboxyl esters, phosphates and phosphate esters. The hydrolysis may be done by chemical reactions conditions such as base hydrolysis or acid hydrolysis or may be done in vivo by biological processes, such as those catalyzed by a phosphate hydrolysis enzyme. Nonlimiting examples of hydrolysable group include groups linked with an ester-based linker (—C(O)O— or —OC(O)—), an amide-based linker (—C(O)$NR^{40}$— or —$NR^{40}$C(O)—), or a phosphate-linker (—P(O)($OR^{40}$)—O—, —O—P(S)($OR^{40}$)—O—, —O—P(S)($SR^{40}$)—O—, —S—P(O)($OR^{40}$)—O—, —O—P(O)($OR^{40}$)—S—, —S—P(O)($OR^{40}$)—S—, —O—P(S)($OR^{40}$)—S—, —S—P(S)($OR^{40}$)—O—, —O—P(O)($R^{40}$)—O—, —O—P(S)($R^{40}$)—O—, —S—P(O)($R^{40}$)—O—, —S—P(S)($R^{40}$)—O—, —S—P(O)($R^{40}$)—S—, or —O—P(S)($R^{40}$)—S—) where $R^{40}$ can be hydrogen or alkyl.

"Alkyl" refers to alkyl groups having from 1 to 12 carbon atoms, preferably 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "$C_x$ alkyl" refers to an alkyl group having x carbon atoms, wherein x is an integer, for example, $C_3$ refers to an alkyl group having 3 carbon atoms.

"Alkenyl" refers to straight or branched hydrocarbyl groups having from 2 to 12 carbon atoms, preferably 2 to 6 carbon atoms and more preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 12 carbon atoms, preferably 2 to 6 carbon atoms and more preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Alkoxy" refers to the group —O-alkyl wherein alkyl is as defined herein. Alkoxy includes, by way of example, methoxy, ethoxy, n-propoxy, iso-propoxy, n-butoxy, t-butoxy, sec-butoxy, n-pentoxy and the like.

"Acyl" refers to the groups $R^{41}$—C(O)—, wherein $R^{41}$ is selected from the group consisting of hydrogen, alkyl, cycloalkyl, aryl, heteroaryl, and heterocyclic, wherein alkyl, cycloalkyl, aryl, heteroaryl, and heterocyclic are as defined herein and are optionally substituted with 1 to 5 substituents independently selected from the group consisting of halo, $C_1$ to $C_3$ alkyl, hydroxyl, and $C_1$ to $C_3$ alkoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

"Aryloxy" refers to the group —O-aryl wherein aryl is as defined herein. Aryloxy includes, by way of example, methoxy, ethoxy, n-propoxy, iso-propoxy, n-butoxy, t-butoxy, sec-butoxy, n-pentoxy and the like.

"Carboxyl" refers to —COOH or salts thereof.

"Carboxyl esters" refers to the groups —C(O)O—$R^{42}$, wherein $R^{42}$ is selected from the group consisting of hydrogen, alkyl, cycloalkyl, aryl, heteroaryl, and heterocyclic, wherein alkyl, cycloalkyl, aryl, heteroaryl, and heterocyclic are as defined herein and are optionally substituted with 1 to 5 substituents independently selected from the group consisting of halo. $C_1$ to $C_3$ alkyl, hydroxyl, and $C_1$ to $C_3$ alkoxy.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, and furyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Alkylene" refers to a divalent radical of an alkyl group. "Methylene" refers to the group —CH$_2$—.

"Arylene" refers to a divalent radical of an aryl group. "Phenylene" refers to the divalent phenyl group —C$_6$H$_4$—.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "monophosphate" refers to the group —P(O)(OH)$_2$.

As used herein, the term "diphosphate" refers to the group —P(O)(OH)—OP(O)(OH)$_2$.

As used herein, the term "triphosphate" refers to the group —P(O)(OH)—(OP(O)(OH))$_2$OH.

It is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Pharmaceutically acceptable salt" refers to pharmaceutically acceptable salts, including partial salts, of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, lactate, succinate, citrate, salicylate, malate, maleate, oxalate, phosphate, phosphite, sulfate, nitrate, perchlorate, aconitate, thalate, embonate, enanthate, and the like.

"Pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

As used herein, the term "therapeutically effective amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
preventing or protecting against the disease or condition, that is, causing the clinical symptoms not to develop, for example, in a subject at risk of suffering from such a disease or condition, thereby substantially averting onset of the disease or condition;
inhibiting the disease or condition, that is, arresting or suppressing the development of clinical symptoms; and/or
relieving the disease or condition that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" refers to mammals and includes humans and non-human mammals.

2. Compounds

This invention is relates to noribogaine derivative compounds. Such compounds are contemplated as being useful in treating pain and/or drug dependency. Accordingly, in one of its composition aspects, this invention is directed to a compound or a pharmaceutically acceptable salt thereof wherein said compound is represented by Formula IA or Formula IB, or a pharmaceutically acceptable salt of each thereof:

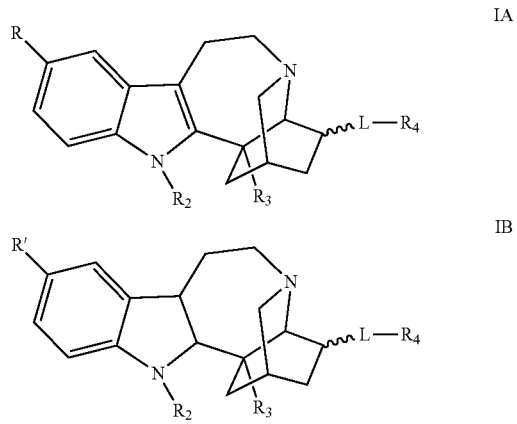

wherein
R is $OR^1$ or $C_1$-$C_{12}$ alkyl optionally substituted with 1 to 5 $R^9$;
$R^1$ is selected from the group consisting of hydrogen, —C(O)OX, —SO$_2$OR$^{10}$, a monophosphate, a diphosphate, a triphosphate, and —C(O)N(Y)$_2$ where X is $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$ heteroaryl having 1 to 4 heteroatoms and which is optionally substituted with 1 to 5 $R^9$, $C_1$-$C_{10}$ heterocyclic having 1 to 4 heteroatoms and which is optionally substituted with 1 to 5 $R^9$, or where each Y, together with the nitrogen atom bound thereto form either a $C_1$-$C_6$ heterocyclic having 1 to 4 heteroatoms and which is optionally substituted with 1 to 5 $R^9$, or a $C_1$-$C_6$ heteroaryl having 1 to 4 heteroatoms and which is optionally substituted with 1 to 5 $R^9$;
R' is halo, $OR^{20}$, or $C_1$-$C_{12}$ alkyl optionally substituted with 1 to 5 $R^9$:
$R^{20}$ is selected from the group consisting of hydrogen, —C(O)X, —C(O)OX and —C(O)N(Y)$_2$ where X and Y are defined as above;
$R^2$ is hydrogen, —SO$_2$OR$^{10}$, a monophosphate, a diphosphate, or a triphosphate;
$R^3$ is selected from the group consisting of hydrogen, —(CH$_2$)$_m$OR$^7$, —CR$^6$(OH)R$^7$, —(CH$_2$)$_m$CN, —(CH$_2$)$_m$COR$^7$, —(CH$_2$)$_m$CO$_2$R$^7$, —(CH$_2$)$_m$C(O)NR$^6$R$^7$, —(CH$_2$)$_m$C(O)NR$^6$NR$^7$R$^7$, —(CH$_2$)$_m$C(O)NR$^6$NR$^7$C(O)R$^8$, and —(CH$_2$)$_m$NR$^6$R$^7$;
m is 0, 1, or 2;
L is a bond or $C_1$-$C_{12}$ alkylene;
$R^4$ is selected from the group consisting of $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;
$X^2$ is selected from the group consisting of O and S;
$Y^2$ is $C_1$-$C_4$ alkylene or $C_6$-$C_{10}$ arylene, or a combination thereof;
n is 1, 2, or 3:
$R^6$ and $R^7$ are each independently selected from the group consisting of hydrogen. $C_1$-$C_{12}$ alkyl optionally substituted with 1 to 5 $R^9$, $C_1$-$C_6$ heterocycle having 1 to 4 heteroatoms which is optionally substituted with 1 to 5 $R^9$, $C_3$-$C_{10}$ cycloalkyl optionally substituted with 1 to 5

$R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$; or $R^6$ and $R^7$ are joined to form $C_1$-$C_6$ heterocycle having 1 to 4 heteroatoms which is optionally substituted with 1 to 5 $R^9$;

$R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^9$ is selected from the group consisting of $C_1$-$C_4$ alkyl, phenyl, halo, —OH, —$OR^{10}$, —CN, —$COR^{10}$, —$CO_2R^{10}$, —$C(O)NHR^{10}$, —$NR^{10}R^{10}$, —$C(O)NR^{10}R^{10}$, —$C(O)NHNHR^{10}$, —$C(O)NR^{10}NHR^{10}$, —$C(O)NR^{10}NR^{10}R^{10}$, —$C(O)NHNR^{10}C(O)R^{10}$, —$C(O)NHNHC(O)R^{10}$, —$SO_2NR^{10}R^{10}$, —$C(O)NR^{10}NR^{10}C(O)R^{10}$, —$NHC(O)R^{10}$, $C_1$-$C_6$ heterocycle having 1 to 4 heteroatoms optionally substituted with 1 to 5 $R^{10}$, and —$C(O)NR^{10}NHC(O)R^{10}$; and $R^{10}$ is $C_1$-$C_{12}$ alkyl;

provided that:

for the compound of Formula IA, when R is —OH or $C_1$-$C_{12}$ alkyl optionally substituted with 1 to 5 $R^9$, then $R^3$ is hydrogen; and for the compound of Formula IA, when $R^3$ is hydrogen, and -L-$R^4$ is ethyl, then R is not —$OR^1$.

In one embodiment, the compound of Formula IA or IB is represented by Formula IA' and IB' respectively:

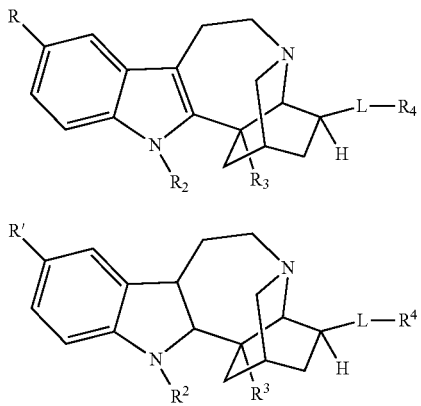

wherein R, $R^2$, $R^3$ and $R^4$ are as described for formula I.

In one embodiment. R is halo, such as fluoro or chloro.

In one embodiment, R is $C_1$-$C_{12}$ alkyl optionally substituted with 1 to 5 $R^9$. In some embodiments, R is $C_1$-$C_{12}$ alkyl optionally substituted with a —$SO_2NR^6R^7$ group.

In another embodiment, R is $OR^1$. In some embodiments, $R^1$ is selected from the group consisting of $C(O)R^5$: —$C(O)NR^5R^5$ and —$C(O)OR^5$; where each $R^5$ is independently selected from the group consisting of hydrogen, alkyl, alkenyl, alkynyl, aryl, heteroaryl, and heterocycle, and wherein the alkyl, alkenyl, alkynyl, aryl, heteroaryl, and heterocycle are optionally substituted with 1 to 5 $R^9$.

In another embodiment, $R^1$ is —$C(O)R^5$, and wherein $R^5$ is $C_1$-$C_{12}$ alkyl or substituted $C_1$-$C_{12}$ alkyl or aryl, which $C_1$ to $C_{12}$ alkyl or aryl is optionally substituted with $C_1$ to $C_3$ alkyl, $C_1$ to $C_3$ alkoxy or aryl. In some embodiments, R is $C_1$-$C_6$ alkyl.

In some embodiments, $R^5$ is selected from the group consisting of methyl, ethyl, n-propyl, n-butyl, n-pentyl, n-hexyl, n-heptyl, n-octyl, n-nonyl, n-decyl, n-undecyl, n-dodecyl, iso-propyl sec-butyl, tert-butyl, phenyl, benzyl, methylbenzyl, and methoxybenzyl.

In some embodiments, $R^1$ is benzoyl.

In some embodiments, $R^1$ is hydrogen.

In some embodiments, $R^2$ is hydrogen. In some embodiments, $R^2$ is $C_1$-$C_{12}$ alkyl optionally substituted with 1 to 5 $R^9$, for example, $CH_2OH$. In some embodiments. $R^2$ is aryl optionally substituted with 1 to 5 $R^9$, for example, phenyl substituted with a halo group. In some embodiments, $R^2$ is —$C(O)R^5$, such as —$C(O)CH_2CH_2N(CH_3)_2$. In some embodiments, $R^2$ is —$C(O)NR^5R^5$, such as —$C(O)NHCH_3$ or $C(O)NHCH_2CH_2N(CH_3)_2$. In some embodiments, $R^2$ is —$C(O)OR^5$, for example, —$C(O)OCH_3$ or —$C(O)OCH_2CH_2N(CH_3)_2$.

In some embodiments, $R^3$ is hydrogen or —$CH_2OH$. In some embodiments, $R^3$ is —$CO_2R^7$.

In some embodiments, L-$R^4$ is not ethyl. In some embodiments, L-$R^4$ is not alkyl. In some embodiments, when R is $OR^1$, L-$R^4$ is not ethyl. In some embodiments, when R is $OR^1$, L-$R^4$, is not alkyl.

In some embodiments, L is $C_1$-$C_6$ alkylene.

In some embodiments, $R^4$ is —X—$R^7$.

In some embodiments, X is O.

In some embodiments, $R^4$ is selected from the group consisting of hydrogen, $C_1$-$C_{12}$ alkyl, —$CH_2Ph$, and —$C(O)OR^7$.

In some embodiments, $R^4$ is —$NH_2$, —$CH_2OCH_2CH_2OCH_3$ or —$OCH_3$.

In some embodiments, the compound is selected from the group consisting of:

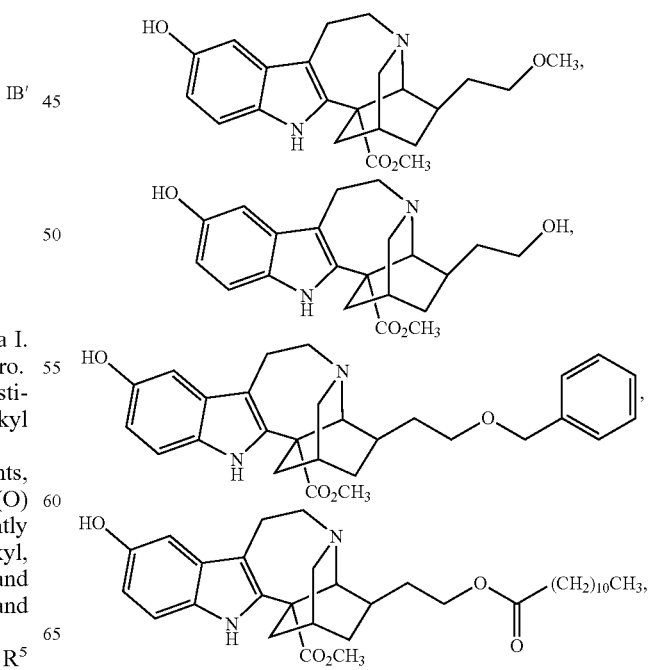

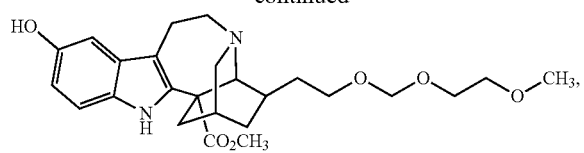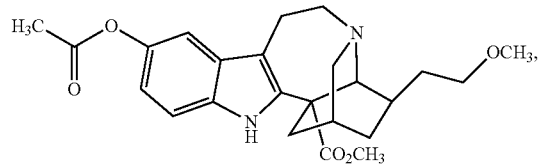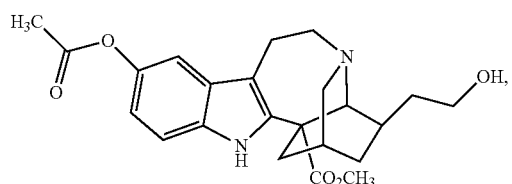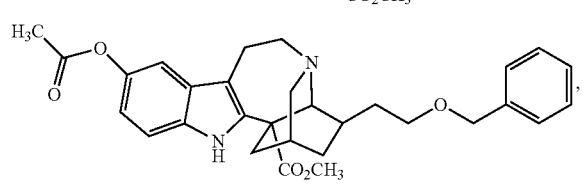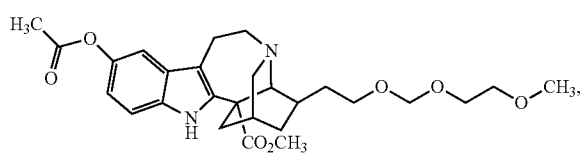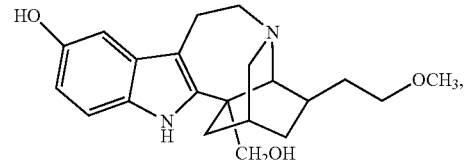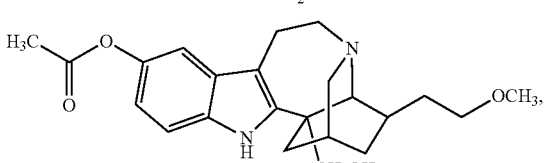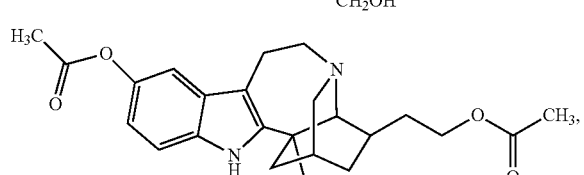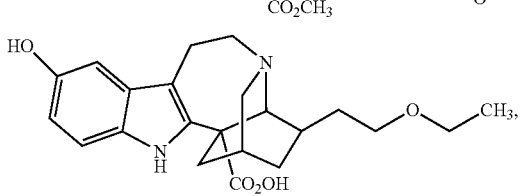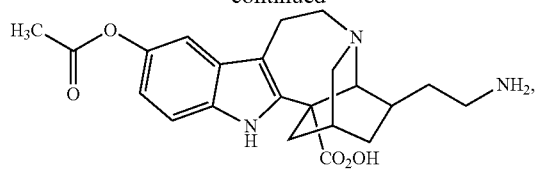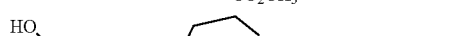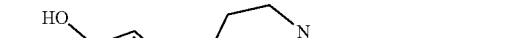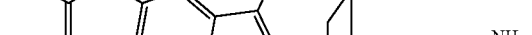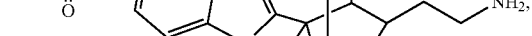

-continued

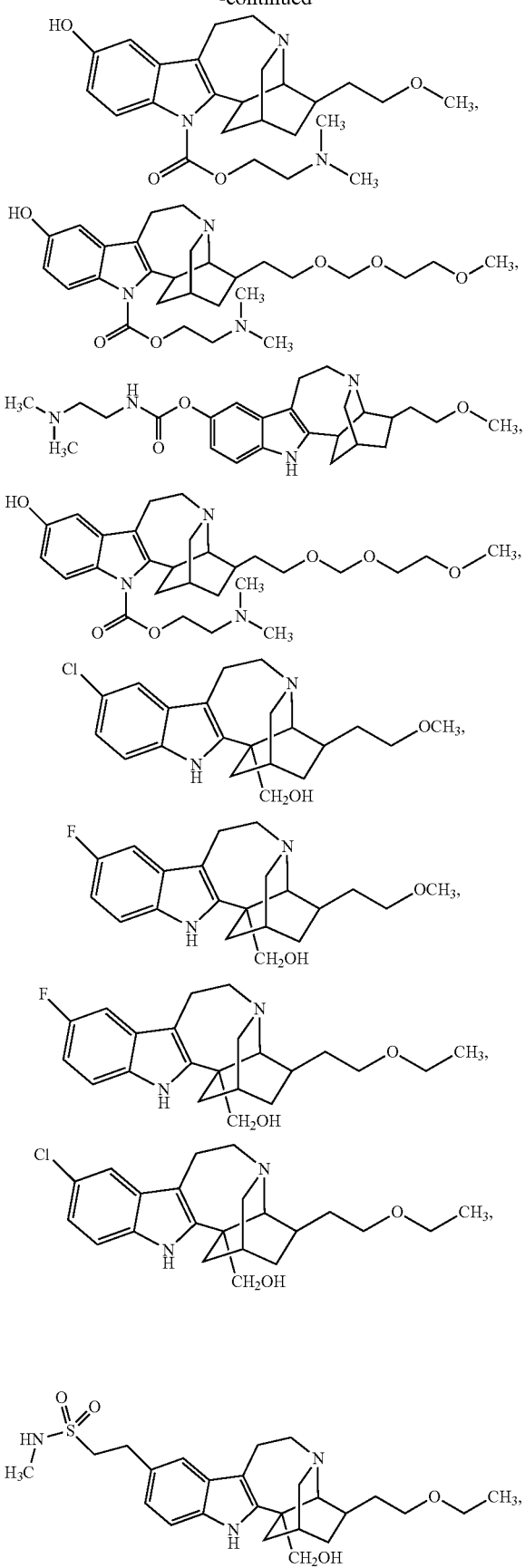

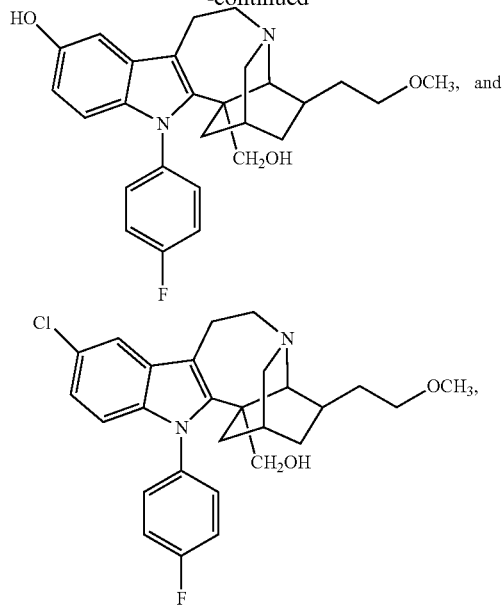

or a pharmaceutically acceptable salt thereof.

In a further embodiment, this invention is directed to a compound or a pharmaceutically acceptable salt thereof wherein said compound is represented by Formula IIA or Formula IIB, or a pharmaceutically acceptable salt of each thereof:

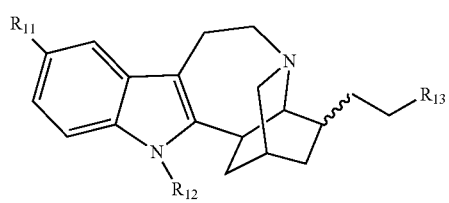

IIA

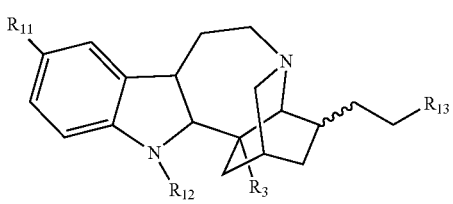

IIB wherein
$R^{11}$ is halo, —OH, —SH, —NH$_2$, —S(O)$_2$N(R$^{16}$)$_2$, —X$^1$-L$^1$-R$^{17}$, —X$^1$-L-R$^{18}$, —X$^1$-L$^1$-R$^{19}$, or —X$^1$-L$^1$-CHR$^{17}$R$^{18}$, where X$^1$ is O, S or NR$^{16}$, or —O-Q, where Q is —SO$_2$—(C$_1$-C$_{12}$ alkyl), a monophosphate, a diphosphate, or a triphosphate;

$L^1$ is alkylene, arylene, —C(O)-alkylene, —C(O)-arylene, —C(O)O-arylene, —C(O)O— alkylene, —C(O)NR$^{19}$-alkylene, —C(O)NR$^{19}$-arylene, —C(NR$^{19}$)NR$^{19}$-alkylene or —C(NR$^{19}$)NR$^{19}$-arylene, wherein L$^1$ is configured such that —O-L$^1$-R$^{17}$ is —OC(O)-alkylene-R$^{17}$, —OC(O)O-arylene-R$^{17}$, —OC(O)O-alkylene-R$^{17}$, —OC(O)-arylene-R$^{17}$, —OC(O)NR$^{19}$-alkylene-R$^{17}$, —OC(O)NR$^{19}$-arylene-R$^{17}$, —OC(NR$^{19}$)NR$^{19}$-alkylene-R$^{17}$ or —OC(NR$^{19}$)NR$^{19}$-arylene-R$^{17}$, and wherein the alkylene and arylene are optionally substituted with 1 to 2 R$^{15}$;

$R^{12}$ is hydrogen, —S(O)$_2$OR$^{19}$, —S(O)$_2$R$^{19}$, —C(O)R$^{14}$, —C(O)NR$^{14}$R$^{14}$, —C(O)OR$^{14}$, C$_1$-C$_{12}$ alkyl optionally substituted with 1 to 5 R$^{15}$, C$_1$-C$_{12}$ alkenyl optionally substituted with 1 to 5 R$^{15}$, aryl optionally substituted with 1 to 5 R$^{15}$, —SO$_2$—(C$_1$-C$_{12}$ alkyl), a monophosphate, a diphosphate, or a triphosphate;

$R^{13}$ is hydrogen, halo, —OR$^{16}$, —CN, C$_1$-C$_{12}$ alkyl, C$_1$-C$_{12}$ alkoxy, aryl or aryloxy, where the alkyl, alkoxy, aryl, and aryloxy are optionally substituted with 1 to 5 R$^5$;

each $R^{14}$ is independently selected from the group consisting of hydrogen, C$_1$-C$_{12}$ alkyl, C$_2$-C$_{12}$ alkenyl, C$_2$-C$_{12}$ alkynyl, aryl, heteroaryl, and heterocycle, and wherein the alkyl, alkenyl, alkynyl, aryl, heteroaryl, and heterocycle are optionally substituted with 1 to 5 R$^{15}$;

$R^{15}$ is selected from the group consisting of phenyl, halo, —OR$^{16}$, —CN, —COR$^{16}$, —CO$_2$R$^{16}$, —NR$^{16}$R$^{16}$, —NR$^{16}$C(O)R$^{16}$, —NR$^{16}$SO$_2$R$^{16}$, —C(O)NR$^{16}$R$^{16}$, —C(O)NR$^{16}$NR$^{16}$R$^{16}$, —SO$_2$NR$^{16}$R$^{16}$ and —C(O)NR$^{16}$NR$^{16}$C(O)R$^{16}$;

each $R^{16}$ is independently hydrogen or C$_1$-C$_{12}$ alkyl optionally substituted with from 1 to 3 halo;

$R^{17}$ is hydrogen, —C(O)R$^{19}$, —C(O)OR$^{19}$, —C(O)N(R$^{19}$)$_2$ or —N(R$^{19}$)C(O)R$^{19}$;

$R^{18}$ is hydrogen, —N(R$^{19}$)$_2$, —C(O)N(R$^{19}$)$_2$, —C(NR$^{19}$)N(R$^{19}$)$_2$, —C(NSO$_2$R$^{19}$)N(R$^{19}$)$_2$, —NR$^{19}$C(O)N(R$^{19}$)$_2$, —NR$^{19}$C(S)N(R$^{19}$)$_2$, —NR$^{19}$C(NR$^{19}$)N(R$^{19}$)$_2$, —NR$^{19}$C(NSO$_2$R$^{19}$)N(R$^{19}$)$_2$ or tetrazole; and each $R^{19}$ is independently selected from the group consisting of hydrogen, C$_1$-C$_{12}$ alkyl and aryl;

provided that:
for the compound of Formula IIA:
when $R^{12}$ and $R^{13}$ are hydrogen, then $R^{11}$ is not hydroxy;
when $R^{13}$ is hydrogen, R is —O-L$^1$-R$^{17}$, —O-L$^1$-R$^{18}$, —O-L$^1$-R$^{19}$, and L$^1$ is alkylene, then —O-L$^1$-R$^{17}$, —O-L$^1$-R$^{18}$, —O-L$^1$-R$^{19}$ are not methoxy; and
when $R^{13}$ is hydrogen, X$^1$ is O, L is —C(O)-alkylene, —C(O)-arylene, —C(O)O-arylene, —C(O)O-alkylene, —C(O)NR$^{19}$-alkylene, or —C(O)NR$^{19}$-arylene, then none of R$^{17}$, R$^{18}$ or R$^{19}$ are hydrogen.

In one embodiment, the compound of Formula II is represented by Formula IIC or Formula IID, or a pharmaceutically acceptable salt of each thereof:

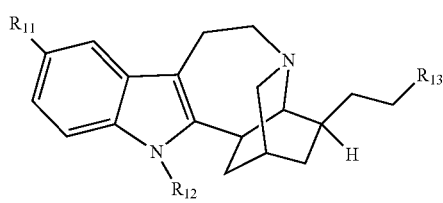

IIC

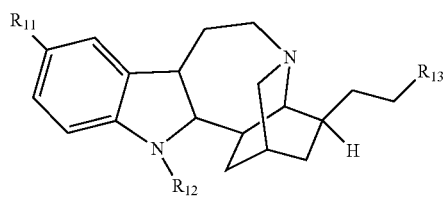

IID

In one embodiment of the compounds of Formula IIA, IIB, IIC, or IID, $R^{11}$ is halo. In certain embodiments of the compounds of Formula IIA, IIB, IIC, or IID, $R^{11}$ is bromo. In certain embodiments, $R^{11}$ is chloro. In certain embodiments of the compounds of Formula IIA, IIB, IIC, or IID, $R^{11}$ is fluoro. In certain embodiments, $R^{11}$ is iodo.

In one embodiment of the compounds of Formula IIA, IIB, IIC, or IID, $R^{11}$ is —OH, —O-L$^1$-R$^{17}$, —O-L$^1$-R$^{18}$, —O-L$^1$-R$^{19}$ or —O-L$^1$-CHR$^{17}$R$^{18}$. In one embodiment of the compounds of Formula I or IIA I, $R^{11}$ is —SH, —S-L$^1$-R$^{17}$, —S-L$^1$-R$^{18}$, —S-L$^1$-R$^{19}$ or —S-L$^1$-CHR$^{17}$R$^{18}$. In one embodiment of the compounds of Formula II or IIA, $R^{11}$ is —NH$_2$, —NR$^{16}$-L$^1$-R$^{17}$, —NR$^{16}$-L$^1$-R$^{18}$, —NR$^{16}$-L$^1$-R$^{19}$ or —NR$^{16}$-L$^1$-CHR$^{17}$R$^{18}$. In one embodiment of the compounds of Formula IIA, IIB, IIC, or IID, $R^{11}$ is —S(O)$_2$N(R$^{16}$)$_2$.

In one embodiment of the compounds of Formula IIA, IIB, IIC, or IID, $R^{11}$ is —Cl, —Br, —I, —OC(O)CH$_2$CH$_3$, —OC(O)CH$_2$Ph, —OC(O)OCH$_2$CH$_3$, —OC(O)OCH$_2$Ph, —OC(O)NH(CH(CH$_3$)Ph), —OC(NPh)NHCH$_2$CH$_3$, —OC(O)NHCH$_2$Ph, —NH$_2$, —NHC(O)C(CH$_3$)$_3$, —NHC(O)CF$_3$, —NHC(O)CH$_2$Ph, —NHC(O)OCH$_2$Ph, —NHC(O)NH(CH(CH$_3$)Ph), —SH, —SC(O)OCH$_2$Ph, —SC(O)NH(CH(CH$_3$)Ph), —SC(O)CH$_2$CH$_2$OP(O)(OH)$_2$, —OC(O)CH$_2$CH$_2$CH(NH$_2$)(CO$_2$H), —O-(2-OH—C$_6$H$_3$)CH$_2$CH(NH$_2$)(CO$_2$H) or —NHC(O)CH$_2$CH$_2$CH(NH$_2$)(CO$_2$H).

In one embodiment of the compounds of Formula IIA, IIB, IIC, or IID, $R^{12}$ is hydrogen.

In one embodiment of the compounds of Formula IIA, IIB, IIC, or IID, $R^{12}$ is —CH$_2$CH$_3$, —CH$_2$CHCH$_2$, —CH$_2$Ph, —C(O)O(CH$_2$)$_2$N(CH$_3$)$_2$ or —C(O)CH$_2$(CH$_2$)$_2$SO$_2$N(CH$_3$)$_2$.

In one embodiment of the compounds of Formula IIA, IIB, IIC, or IID, $R^3$ is hydrogen.

In one embodiment of the compounds of Formula IIA, IIB, IIC, or IID, $R^3$ is halo. In certain embodiments of the compounds of Formula IIA, IIB, IIC, or IID, $R^3$ is bromo. In certain embodiments of the compounds of Formula IIA, IIB, IIC, or IID, $R^3$ is fluoro.

In one embodiment of the compounds of Formula IIA, IIB, IIC, or IID, $R^3$ is —OCH$_3$, —OCH$_2$CH$_3$, —OCH$_2$Ph or —CN.

In some embodiments of the compounds of Formula IIA, JIB, IIC, or IID, the compound is represented by formula IIE selected from Table 1:

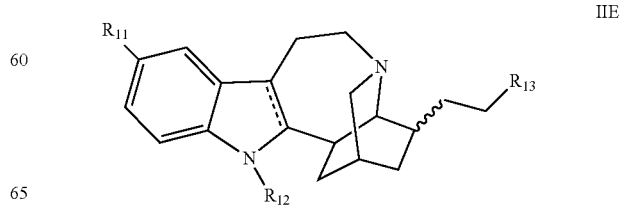

IIE

TABLE 1

| No. | $R^{11}$ | $R^{12}$ | $R^{13}$ | ≡≡≡ |
|---|---|---|---|---|
| 1 | Cl | H | H | double bond |
| 2 | Br | H | H | double bond |
| 3 | I | H | H | double bond |
| 4 | —OC(O)CH$_2$CH$_3$ | H | H | double bond |
| 5 | —OC(O)CH$_2$Ph | H | H | double bond |
| 6 | —OC(O)OCH$_2$CH$_3$ | H | H | double bond |
| 7 | —OC(O)OCH$_2$Ph | H | H | double bond |
| 8 | —OC(O)NH(CH(CH$_3$)Ph) | H | H | double bond |
| 9 | —OC(NPh)NHCH$_2$CH$_3$ | H | H | double bond |
| 10 | —OC(O)NHCH$_2$Ph | H | H | double bond |
| 11 | —NH$_2$ | H | H | double bond |
| 12 | —NHC(O)C(CH$_3$)$_3$ | H | H | double bond |
| 13 | —NHC(O)CF$_3$ | H | H | double bond |
| 14 | —NHC(O)CH$_2$Ph | H | H | double bond |
| 15 | —NHC(O)OCH$_2$Ph | H | H | double bond |
| 16 | —NHC(O)NH(CH(CH$_3$)Ph) | H | H | double bond |
| 17 | —SH | H | H | double bond |
| 18 | —SC(O)OCH$_2$Ph | H | H | double bond |
| 19 | —SC(O)NH(CH(CH$_3$)Ph) | H | H | double bond |
| 20 | —SC(O)CH$_2$CH$_2$OP(O)(OH)$_2$ | H | H | double bond |
| 21 | —OC(O)CH$_2$CH$_2$CH(NH$_2$)(CO$_2$H) | H | H | double bond |
| 22 | —O-(2-OH—C$_6$H$_3$)CH$_2$CH(NH$_2$)(CO$_2$H) | H | H | double bond |
| 23 | —NHC(O)CH$_2$CH$_2$CH(NH$_2$)(CO$_2$H) | H | H | double bond |
| 24 | —OH | H | H | single bond |
| 25 | Cl | H | H | single bond |
| 26 | Br | H | H | single bond |
| 27 | I | H | H | single bond |
| 28 | —OC(O)CH$_2$CH$_3$ | H | H | single bond |
| 29 | —OC(O)OCH$_2$Ph | H | H | single bond |
| 30 | —OC(O)NH(CH(CH$_3$)Ph) | H | H | single bond |
| 31 | —OC(O)NHCH$_2$Ph | H | H | single bond |
| 32 | —NH$_2$ | H | H | single bond |
| 33 | —NHC(O)C(CH$_3$)$_3$ | H | H | single bond |
| 34 | —NHC(O)NH(CH(CH$_3$)Ph) | H | H | single bond |
| 35 | —SH | H | H | single bond |
| 36 | —SC(O)OCH$_2$Ph | H | H | single bond |
| 37 | —OH | —CH$_2$CH$_3$ | H | double bond |
| 38 | —OH | —CH$_2$CHCH$_2$ | H | double bond |
| 39 | —OH | —CH$_2$Ph | H | double bond |
| 40 | —OH | —C(O)O(CH$_2$)$_2$N(CH$_3$)$_2$ | H | double bond |
| 41 | —OH | —C(O)CH$_2$(CH$_2$)$_2$SO$_2$N(CH$_3$)$_2$ | H | double bond |
| 42 | —OH | H | —OCH$_2$CH$_3$ | double bond |
| 43 | —OH | H | —OCH$_2$Ph | double bond |
| 44 | —OH | H | —CF$_3$ | double bond |
| 45 | —OH | H | —OH | double bond |
| 46 | —OH | H | —CN | double bond | or a pharmaceutically acceptable salt thereof.

In some embodiments of the compounds of Formula IA, the compound is represented by Formula IC selected from Table 2:

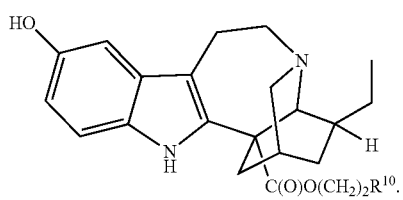

IC

TABLE 2

| No. | $R^{10}$ |
|---|---|
| 47 | NMe$_2$ |
| 48 | OH |
| 49 | NHC(O)Me |
| 50 | OMe |
| 51 | azetidin-1-yl |
| 52 | pyrrolidin-1-yl |
| 53 | 4-methylpiperazin-1-yl |
| 54 | morpholin-4-yl |

In certain embodiments, the compound of Formula IA, IB, IC, IIA, IIB, IIC, or IID, is the hydrochloride salt. In another embodiment, the compound of Formula IA, IB, IC, IIA, IIB, IIC, or IID, is the hydrobromide salt. In another embodiment, the compound of Formula IA, IB, IC, IIA, IIB, IIC, or IID, is the phosphate salt. In another embodiment, the compound of Formula IA, IB, IC, IIA, IIB, IIC, or IID, is the sulfate salt.

3. Methods of Use

Treatment of Pain

In one of its method aspect, the present invention is directed to a method for treating a pain in a patient which method comprises administering to said patient a compound of this invention or a pharmaceutically acceptable salt thereof or a pharmaceutical composition comprising a compound of this invention and a pharmaceutically acceptable excipient. The pain can be any type of pain including, but not limited to neuropathic or nociceptive pain, and various types thereof including somatic, visceral and phantom pain.

Treatment of Addiction

In another of its method aspect, the present invention is directed to a method for treating addiction in a patient which method comprises administering to said patient a compound of this invention or a pharmaceutically acceptable salt thereof or a composition comprising a compound of this invention and a pharmaceutically acceptable excipient.

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, it is contemplated that treatment with a compound of this invention decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

The invention is also directed to a method for treating drug addiction (involving drug dependency or drug abuse) during withdrawal therapy by administering a compound of this invention to a patient at a dosage sufficient to reduce or eliminate one or more symptoms associated with withdrawal. Such symptoms include nausea, vomiting, anxiety, abdominal cramps, muscle pain, chills and headache. In addition, treatment with a compound of this invention is contemplated to decrease the drug cravings normally experienced by addicts after cessation of the self administration of the abused substance, for example, narcotics such as heroin and methadone. However, compounds of this invention are contemplated to be also useful in treating patients addicted to cocaine, alcohol, amphetamines and combinations of these drugs. Compounds of this invention may be administered to patients suffering from drug dependence or abuse in conjunction with an opioid antagonist such as naloxone, naltrexone or nalorphine, for example, at a concentration of between 0.15 mg and 0.5 mg for each mg of the compound of this invention administered.

Treatment of Nicotine Addiction

Tobacco use remains a major health problem despite widespread knowledge of the damaging consequences. Although current smoking cessation therapies, including nicotine replacement, buproprion, and varenicline, have had some success, they are inadequate since only a fraction (30-40%) of smokers who try these medications abstain from tobacco use. Consequently, more effective or add-on therapies are needed. Nicotine is one of the most addictive drugs that is widely used; 95% or more of its users with a strong desire to stop using relapse within one year. Chronic nicotine use leads to physiological changes in nAChR function and expression, including upregulation of high-affinity a4b2 nAChRs expression and reduced receptor function due to desensitization. In addition to the reinforcing properties of nicotine, the physical discomfort associated with nicotine withdrawal includes severe cravings, anxiety, dysphoria, and autonomic dysfunction. Although it is known that the reinforcing and addictive effects of nicotine are due to is actions on nAChRs, the identification of which nAChR subtypes play a role in the various aspects of nicotine dependence/withdrawal, and their validation as drug targets for medication development remains a complex area of investigation. The a4 subunit is implicated in nicotine reinforcement, sensitization and the development of tolerance. While the development of tolerance is not regulated by a7 nAChRs, a recent study indicated that that these receptors may control the severity of the withdrawal symptoms. Thus, there is a complex regulatory interplay of nAChRs, which likely contribute to nicotine dependence/withdrawal.

Neuronal nicotinic acetylcholine receptors (nAChRs) have been a target for CNS drug discovery efforts for the past two decades. Mounting evidence suggests that the addictive effects of nicotine, occur through interaction with its receptor in the mesolimbic dopamine system. However, the molecular identity of the nicotinic receptors responsible for drug seeking behavior, their cellular and subcellular location and the mechanisms by which these receptors initiate and maintain nicotine addiction are poorly defined. While nicotine and related natural products have been used for smoking cessation in various formulations (e.g., gum, spray, patches), it was only in 2006 with Pfizer's launch of varenicline (Chantix™) for smoking cessation that a new chemical entity (NCE) targeting neuronal AChRs was approved for this condition. Varenicline is a weak partial agonist for a4b2 nAChR subtypes and a less potent agonist at a7 subtypes. A serendipitous finding in aiding smoking cessation is the discovery that the atypical anti-depressant buproprion, whose mechanism of action as a non-competitive antagonist of a3b4 nAChRs and antidepressant activity underlie its efficacy. Buproprion analogs are under development as potential pharmacotherapies for smoking cessation. Second generation noribogaine analogs targeted to a3b4 nAChRs offer a novel synthetic route for development of potential small molecules to treat tobacco addiction and other SRDs.

Recent genetic association studies show that single nucleotide polymorphisms (SNPs) in the gene cluster CHRNA5/A3/B4, encoding for the a3, a5 and b4 nAChR subunits are associated with increased risk for heavy smoking, inability to quit, and increased sensitivity to nicotine. Furthermore, a3b4 nAChRs or other b4 containing receptors have been suggested to be involved in nicotine withdrawal. The expression of the a3b4 AChR is restricted to a few discrete brain areas, including the medial habenula and interpeduncular nucleus, and autonomic ganglia. Recent behavioral studies in genetic mouse models suggest that disrupted function and/or expression of the a3b4 (and a5 subunits) in the habenulo-IPN tract may be critical for regulating nicotine intake and the addictive properties of this substance. The habenula-interpeduncular system and a3b4 nAChR subunits in this pathway play an important role in nicotine withdrawal. The compounds of this invention were found to inhibit a3b4 nAChRs.

In another of its method aspect, the present invention is directed to a method of treating nicotine addiction in a patient which method comprises administering an effective amount of a compound of this invention or a pharmaceutically acceptable salt thereof or a composition comprising a compound of this invention and a pharmaceutically acceptable excipient to a patient in need thereof.

In another of its method aspect, the present invention is directed to a method of inhibiting a3b4 nicotinic acetylcholine receptors which method comprises administering an effective amount of a compound of this invention or a pharmaceutically acceptable salt thereof or a composition comprising a compound of this invention and a pharmaceutically acceptable excipient.

Combination Therapy

Compounds of this invention maybe used alone or in combination with other compounds to treat pain and/or addiction. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, a compound of this invention can be used as an adjunct to conventional drug withdrawal therapy, specifically providing for the administration of a compound of this invention with one or more opioid antagonists.

4. Compositions

In another aspect, this invention is also directed to pharmaceutical compositions comprising a pharmaceutically acceptable excipient and a compound of this invention or mixtures of one or more of such compounds.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980). Intranasal administration is an effective method for delivering a therapeutic agent directly to the respiratory tract, where the therapeutic agent may be quickly absorbed.

The compositions are comprised of in general, a compound of this invention or a mixture thereof in combination with at least one pharmaceutically acceptable excipient. Acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

The amount of the compound in a formulation can vary within the full range employed by those skilled in the art. Typically, the formulation will contain, on a weight percent (wt %) basis, from about 0.01 to 99.99 wt % of a compound of this invention based on the total formulation, with the balance being one or more suitable pharmaceutical excipients. Preferably, the compound is present at a level of about 1 to 80 wt %. In a liquid composition, a compound of this invention should generally be present in such compositions at a concentration of between about 0.1 and 20 mg/ml. When either naloxone or naltrexone is combined with a compound of this invention, they should be present at 0.05 to 0.5 mg for each mg of the compound of this invention.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Generally, the compound of this invention is administered in an effective amount. It is contemplated that the dosage required for treating pain or addition, or a combination thereof may differ according to the condition(s) being treated, however, the dosing regimen can be readily determined by the attending clinician based on the desired treatment. It is contemplated that generally, the dosage of a compound of this invention administered to a patient may be from about 0.01 to about 1000 mg per kg of body weight per day (mg/kg/day), or from 0.05 to 500 mg/kg/day, preferably, from about 0.1 to about 100 mg/kg/day, more preferably from about 0.5 to 50 mg/kg/day. For example, for administration to a 70 kg person, the dosage range would preferably be about 35 to 700 mg per day.

In addition to the methods discussed above, the present invention is directed to a pharmaceutical composition, preferably in unit dose form, comprising a compound of this invention. When administered to a patient, one or more unit doses provide an amount of a compound of this invention effective to treat pain and/or addition.

The amount of the composition administered will depend on a number of factors, including but not limited to the desired final concentration of the compound, the pharmacokinetic and pharmacodynamic properties of the compound, the size, age, and physiological profile of the patient, and the like. The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Determination of dosages is well within the empiric knowledge of persons skilled in the art; nonetheless, it can be appreciated that estimates of final dosages can be made by approximating the concentration of compound necessary to achieve a desired therapeutic activity, such as treatment of pain and/or addiction. Extrapolation to a specified mammalian dosage range, or more particularly a human dosage range is well within the skill of the practitioner.

In some embodiments, compositions are administered in one dosing of a single formulation and in other embodiments, compositions are administered in multiple dosing of a single formulation within a specified time period. In some embodiments, the time period is between about 3 hours to about 6 hours. In other embodiments, the time period is between about 6 hours and 12 hours. In additional embodiments, the time period is between about 12 hours and 24 hours. In yet further embodiments, the time period is between about 24 hours and 48 hours. The administration of separate formulations can be simultaneous or staged throughout a specified time period, such that all ingredients are administered within the specified time period.

The following are examples of the compositions of this invention.

Example 1: Tablet Formulation

The following ingredients are mixed intimately and pressed into single scored tablets.

| Ingredient | Quantity per tablet, mg |
| --- | --- |
| Compound of Formula I | 40 |
| Cornstarch | 50 |
| Croscarmellose sodium | 25 |
| Lactose | 120 |
| Magnesium stearate | 5 |

Example 2: Capsule Formulation

The following ingredients are mixed intimately and loaded into a hard-shell gelatin capsule.

| Ingredient | Quantity per tablet, mg |
| --- | --- |
| Compound of Formula I | 20 |
| Lactose, spray-dried | 148 |
| Magnesium stearate | 2 |

Example 4: Suspension Formulation

The following ingredients are mixed to form a suspension for oral administration (q.s.=sufficient amount).

| Ingredient | Amount |
| --- | --- |
| Compound of Formula I | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co) | 1.0 g |
| flavoring | 0.035 mL |
| colorings | 0.5 mg |
| distilled water | q.s. to 100 mL |

Example 3: Injectable Formulation

The following ingredients are mixed to form an injectable formulation.

| Ingredient | Quantity per tablet, mg |
|---|---|
| Compound of Formula I | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Example 5: Suppositor Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of Formula I | 500 mg |
| Witepsol ® H-15 | balance |

Example 6: Screening Compounds for nAChR Target

Preliminary functional studies performed by Caliper Life Sciences (Hopkinton, Mass.), using the FLIPR® Ca+2 flux assay, demonstrated that noribogaine (12-hydroxyibogamine) was more potent as an antagonist ($IC_{50}$=462 nM) for epibatine induced $Ca^{+2}$ flux in SH-SY5Y cells compared to 18-MC (3.89 μM), where SH-SY5Y cells predominantly express the α3β4 nicotinic receptor subtype. Additional functional studies using HEK293 cells expressing α3β4 nicotinic receptors show that congeners of 18-MC, with identical substituents as shown above, can modulate the rate and recovery of nicotinic receptor desensitization. The FLIPR® Ca+2 flux assay is used with HEK293 cells overexpressing a3b4, a4b2 or a7 to determine the potency and selectivity of the noribogaine congeners. The HEK293 (a3b4, a4b2 and a7) and SH-SY5Y cell lines (a3b4) expressing nAChRs are used. Validated assays optimized with respect to sensitivity, dynamic range, signal intensity and stability for chemical probe validation and SAR refinement are used.

Nicotinic functional assays are performed using the Molecular Devices FLIPR® Calcium 5 Assay Kit. HEK293 cells overexpressing α3β4, α4β2 or α7 (50,000 cells per well in 100 μl growth media) and are plated in clear bottom black walled 96-well microplates and incubated for 24-48 hours at 37° C., 5% $CO_2$ until a 80-90% confluent monolayer is formed. On the day of the assay, 100 μl of Calcium 5 Dye is added to each well. Following addition of dye, cells are incubated at 25° C. for 60 minutes. Following dye loading, 50 μl of a 5× solution of reference or test compound of appropriate concentration range (0.01-30 μM), prepared in 20 mM HEPES pH 7.4 in HBSS, is added to each well. Plates are then transferred to the Molecular Devices Flexstation® which transfers 50 μL of a 5× solution (500 nM) of epibatine to each well to initiate the Ca+2 flux. Additional wells (in quadruplicate) are prepared with no added test or reference ligand for measurement of 100% flux. The RFU (relative fluorescence units) in the presence of the test or reference compounds is then expressed on the percent scale. The percent inhibition of epibatidine induced $Ca^{+2}$ flux is calculated as follows: % inhibition=100%−% RFU (relative fluorescence units). The $IC_{50}$ values for reference and test compounds are obtained by fitting normalized RFU data using Graphpad Prism software.

$^{86}RB^+$ efflux assays are also used to assess whether noribogaine or its analogs have activity as antagonists at human nAChR using naturally or heterologously expressed cell lines and compared to synaptosomal preparations from mouse brain. SHSY cells function only for measures of a3b4, because a7 nAChRs, which are also expressed by these cells inactivate too quickly to detectably contribute to ion influx. $6RB^+$ efflux in the presence of the compounds is used to test for agonist and antagonist activity at hAChRs. Representative concentration curves are obtained to complete the SAR profiling of the compound series. Inhibition of agonist stimulated DA and ACh release are tested in striatal and IPN synaptosomal preparations according to known methods using L-nicotine or cytosine to stimulate release, respectively. $IC_{50}$ values for inhibition of ACh and DA release (μM) are determined from the curve fits of the data with or without test compound present.

TABLE 3

Inhibition of epibatidine-induced calcium response in a3b4 nAChRs-containing cell lines

|  | $IC_{50}$ (uM) SH-SYSY | $IC_{50}$ (uM) A3B4-HEK | $IC_{50}$ (uM) Caliper |
|---|---|---|---|
| Mecamylamine | 0.4 +/− 0.6 | 1.6 +/− 0.6 | 0.3 |
| Noribogaine | 0.3 | 18 +/− 10 | 1 +/− 0.7 |
| 18MC | 3.9 |  | 3.9 |

The results shown in Tables 3 and 4 reveal that addition of a substituent $R^{10}$ at C-18C(O)O(CH$_2$)$_2$ leads to higher affinity for the receptor relative to the unsubstituted parent compound. The highest effect is with N(CH$_3$)$_2$ analog namely, compound 47 and OCH$_3$ analog, compound 50. Reduced potency is seen with NHCOCH$_3$, compound 49. This can be understood on the basis of OCH$_3$ and N(CH$_3$)$_2$ being strong electron donors (Lewis bases and hydrogen bond donors) compared with the NHCO group with lower electron density on the nitrogen atom due to amide resonance.

In these studies, ibogaine, compound 47, and compound 50 were found to be more potent inhibitors than 18-MC (18-methoxycoronaridine) and noribogaine on the epibatidine-induced calcium response in a3b4 nAChRs (left panel; DMX 1001A is noribogaine and OBI.215.21.1 is 18-MC). Compound 47 displayed a better affinity (5-fold) and selectivity (10-fold) for kOR than for mOR in comparison to 18-MC. In comparison to noribogaine, compound 47 gained affinity at kOR (X2), but mainly lost affinity to mOR resulting in a right-ward shift. Compounds 47 and 50 lost affinity for mOR and retained affinity for kOR. These results suggest that compounds 47 and 50 have improved selectivity while maintaining a3b4 activity.

TABLE 4

Evaluation of the relative potency of 18-MC and Noribogaine analogues (compounds 47-50) at a3b4 nAChRs

|  | Ratio from 18-MC |
|---|---|
| Mecamylamine | 0.1 |
| Noribogaine | 0.25 to 1 |
| Ibogaine | 0.07 to 0.26 |
| 18-MC | 1 (4 uM) |
| Compound 47 | 0.5 |
| Compound 48 | 0.8 |

TABLE 4-continued

Evaluation of the relative potency of 18-MC and Noribogaine analogues (compounds 47-50) at a3b4 nAChRs

| | Ratio from 18-MC |
|---|---|
| Compound 49 | 1.1 |
| Compound 50 | 0.2 |

Example 7: Mu and Kappa Opioid Receptor Binding Activity

Noribogaine binds with high affinity (50 nM) to the 5-HT transporter and weak affinity at mu (900 nM) and kappa (1 μM) opioid receptors. At physiologically relevant concentrations, noribogaine only bound to SERT, DAT, mu and kappa opioid receptors (out of a panel of over 50 receptors, transporters, ion channels, second messengers, growth factor receptors and enzymes). The association between cigarette smoking and the presence and severity of suicidal behavior across major psychiatric disorders may be related to lower brain serotonin function in smokers with depression). Noribogaine analogs will likely retain affinity for the 5-HT transporter and we plan to fully characterize their activity in radioligand binding and functional uptake assays (serotonin and DA).

Established radioligand binding methods are used to evaluate the ability of the compounds to block reuptake of scrotonin and dopamine in membrane preparations of synaptosomes. Equilibrium binding affinity values is determined for each compound at opioid receptors (μ and κ subtypes) and biogenic amine transporters (DAT and SERT). Where possible, binding experiments utilize membranes derived from CHO or HEK293 cells engineered to overexpress the human form of the receptor or transporter of interest. Radiolabeling of opioid receptors, and biogenic amine transporters utilizes conventional radioligands, buffers and incubation conditions according to published assays.

Test compounds, reference compounds and the radioligand (Kd value) are added to binding buffer. Assays are run with test or reference compound over a range of concentration (0.0001-10 uM) in triplicate using a 96-well sample plate containing radioligands specific for the target receptor or transporter. Cell membranes at the appropriate concentration are added in a volume of 400 μl in binding buffer. Following mixing on a plate shaker, samples are incubated for 1-2 hours (depending on the transporter or receptor) at 25° C. and filtered onto 96-well Unifilters (pre-treated with 0.3% polyethyleneimine) using a Filtermate harvester. Bound radioactivity is counted in a Microbeta scintillation counter. Total bound radioactivity is estimated from triplicate wells containing no test or reference compound, together with nonspecific binding and filter blanks. The average bound radioactivity in the presence of the test compounds is expressed % inhibition=100%−% radioactivity bound. The $IC_{50}$ and Ki values for test and reference compounds are obtained by fitting normalized CPM data fitted using nonlinear (Graphpad Prism software).

Example 8: CNS Penetration Across the Brain Blood Barrier

Ibogaine, noribogaine, and 18-MC cross the BBB and reach micromolar concentrations in brain. Mice are dosed with compounds. Brain to blood ratios are determined by HPLC and LC/MS/MS analysis following oral administration of the test compounds in mice. Compound pharmacokinetic studies at representative time points are obtained in vivo in mice to demonstrate that the drug crosses the BBB following oral administrations.

5. Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations of these forms are within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4.sup.th Edition), and Larock's Comprehensive Organic Transformations (VCH Publishers Inc., 1989).

Compounds of this invention may be prepared using the starting material Compound 1.1, which may be prepared according to Scheme 2, according to known procedures, such as those described in Bornmann, et al., *J. Org. Chem.*, 57:1752 (1992) and U.S. Pat. No. 6,211,360, which are hereby incorporated by reference in their entirety. Scheme 1 shows an exemplary general process for prepare compounds of this invention. The starting materials for the following reactions are generally known compounds or can be prepared by known procedures.

(trimethylsilyl)ethoxymethyl ether (SEM)) and certain substituted alkyl groups (e.g. benzyl). The need to protect and the types of protecting groups used for the hydroxy and/or the indole nitrogen will depend on the exact reaction conditions and reagents used in subsequent steps, which would

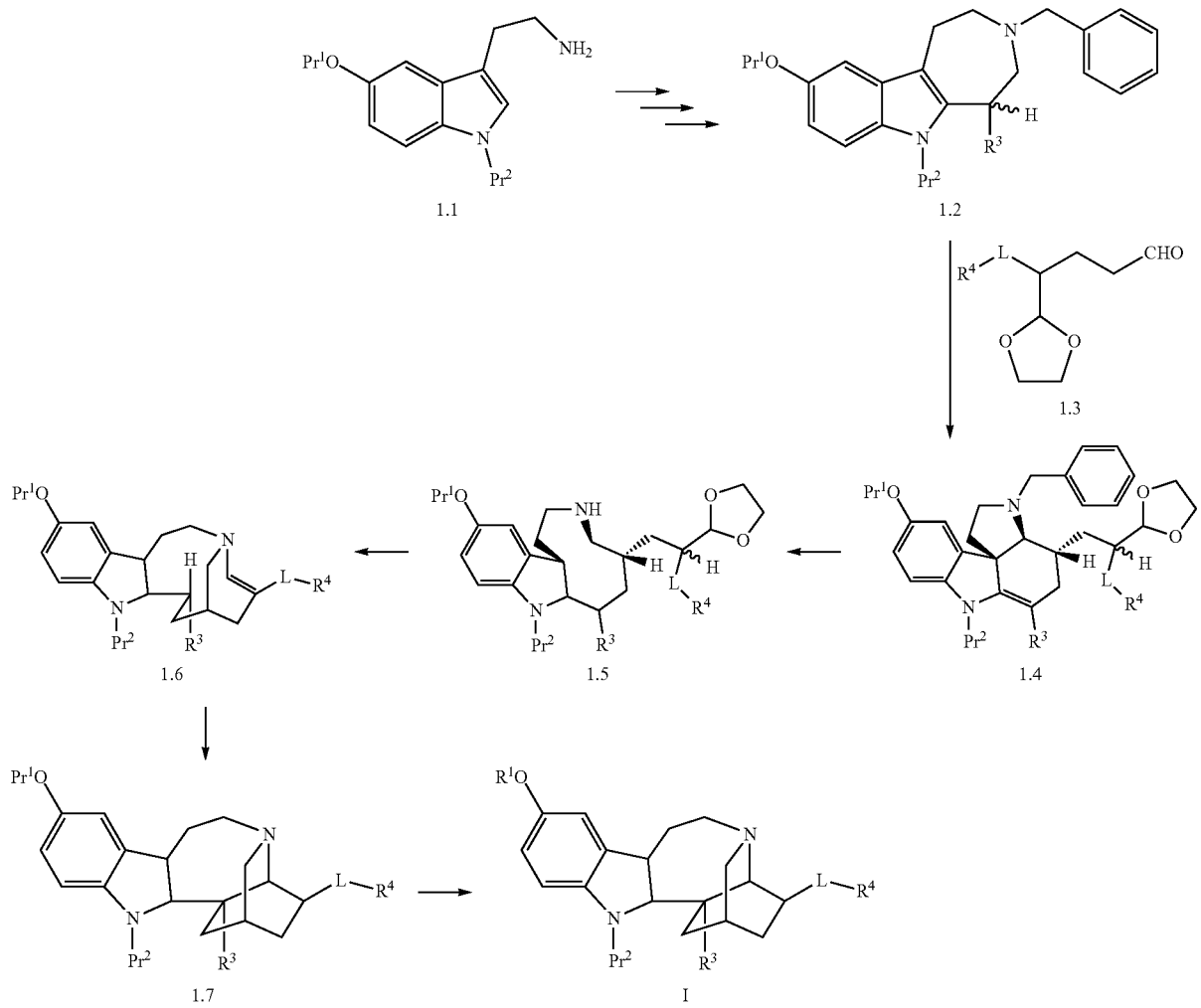

Scheme 1 shows an exemplifying procedure to prepare compounds of Formula I, wherein $R^2$, $R^3$, L and $R^4$ are as defined herein. Compound 1.1, wherein $Pr^1$ is $R^1$ as defined herein or a hydroxy protecting group, and $Pr^2$ is $R^2$ as defined herein or a protecting group for the indole nitrogen, is converted to Compound 1.2 using the procedure described in Kuehne, et al. *J. Org. Chem.* 50:919 (1985). Hydroxyl protecting groups include a hydrolysable group as defined for Formula I, such as —C(O)R, wherein R is as defined herein, and other hydroxyl protecting groups known in the art, such as a benzyl (Bn) group, 2,4-dichlorobenzyl (DCB), methoxymethyl (MOM), tetrahydropyranyl (THP), acyl (such as acetyl (Ac)) or a silyl group, etc. Other suitable hydroxy protecting groups are known in the art. Protecting groups for the indole nitrogen include arylsulfonyl derivatives (e.g. tosyl (Ts)), carbamates (e.g. fluorenylmethyloxycarbonyl (Fmoc) and tert-butyloxycarbonyl (t-BOC), trialkylsilyl groups (e.g. triisopropylsilyl). N,O-acetals (e.g.

be generally known in the art. When $Pr^1$ is $R^1$ and/or $Pr^2$ is $R^2$, they can be retained as part of the final compounds, or may be converted to other groups as defined in Formula I by methods generally known in the art. When $Pr^1$ and/or $Pr^2$ are other protecting groups, they can be removed under proper deprotection conditions to provide the free hydroxy group and/or free indole nitrogen, which may be further converted to the $R^1$ and/or $R^2$ groups as defined in Formula I.

Compound 1.2 may react with Compound 1.3 to give Compound 1.4 in dry toluene under reflux conditions, and preferably with a Dean-Stark trap with molecular sieves. Compound 1.3 can be prepared by using methods described in U.S. Pat. No. 6,211,360, which is incorporated by reference in its entirety.

Alternatively, Compound 1.2 may react with Compound 1.3 to give a condensation product in an organic solvent, such as alcohol solvents, such as methanol, ethanol, isopropanol, and n-butanol; ester-containing solvents, such as ethyl acetate and isopropyl acetate; ether solvents, such as tetrahydrofuran, diglyme, and dioxane; chlorinate hydrocarbons, such as methylene chloride, chloroform, and carbon tetrachloride; aromatic hydrocarbons, such as benzene, toluene, and xylene; acetonitrile; pyridine; and dimethylformamide. The reaction may proceed under room temperature or under heated conditions, such reflexing conditions. After the condensation reaction, the condensation product is treated in a suitable solvent with an equivalent amount of an appropriate arylalkyl containing a good leaving group, such as an arylalkyl tosylate, an arylalkyl mesylate, or an arylalkyl halide, such as benzyl bromide, for 0.5 to 72 hours, for example, 16 hours, at 50° C. to 120° C., which may be at the reflux temperature of the solvent. Suitable solvents include lower alkanes, such as pentane, hexane, or petroleum ether; aromatic hydrocarbon solvents, such as benzene, toluene, and xylene; alcohols, such as methanol, ethanol, isopropanol, and n-butanol; and ether solvents, such as diethyl ether, diglyme, or tetrahydrofuran.

Treatment of the above product, with an organic-soluble Lewis base, such as triethylamine, produces a transient enamine acrylate of the formula:

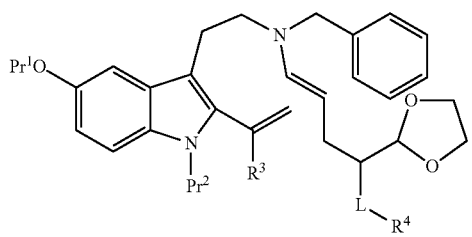

This reaction can proceed in an organic solvent, including alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. This reaction can be conducted at any temperature from room temperature to the boiling point of the solvent, for example, from 50° C. to 70° C. for, for example, from 1 to 10 hours. The transient enamine acrylate spontaneously cyclizes to give Compound 1.4.

Compound 1.4 undergoes reduction with a reducing agent, such as NaBH$_4$, in the presence of acetic acid, under heating conditions, for example, at a temperature of between 80° C. and 110° C., or between 85° C. and 95° C., followed by catalytic hydrogenation in the presence of a catalyst, such as palladium, in a solvent, such as methanol, to provide Compound 1.5.

Hydrolysis of Compound 1.5 under acidic conditions, for example, with glacial acetic acid and/or hydrochloric acid in a solvent, such as MeOH gives Compound 1.6, which undergoes cyclization to give Compound 1.7 in a dry solvent under heating conditions, for example, in dry toluene at 130° C.

Finally, Pr$^1$ and/or Pr$^2$ may be removed under suitable deprotection conditions to provide compounds where R$^1$ and/or R$^2$ are hydrogen. One or both of these hydrogen atoms may be substituted by a desired R$^1$ and/or R$^2$ by reaction with R$^1$Lg and/or R$^2$Lg, wherein Lg is a leaving group, such as a halo group (e.g., chloro, bromo and iodo), sulfonate esters, such as para-toluenesulfonate or tosylate (OTs), hydroxy or alkoxy group. Further manipulations of the R$^1$, R$^2$, R$^3$ and/or R$^4$ to provide other embodiments of this invention are apparent to a person skilled in the art.

In Scheme 2, Compound 2.1 (5-hydroxyindole-3-acetic acid, which is commercially available, for example, from Sigma-Aldrich Corp.) may be protected to give Compound 2.2, wherein Pr$^1$ and Pr$^2$ are as defined above. Compound 2.2 is reduced to the corresponding alcohol Compound 2.3, using a reducing agent, such as lithium aluminumhydride. Reduction of Compound 2.2 to Compound 2.3 may optionally conducted via an intermediate aldehyde compound. The hydroxy group of Compound 2.3 is converted to a leaving group Lg$^2$, such as a halo group (e.g., chloro, bromo and iodo), sulfonate esters, such as para-toluenesulfonate or tosylate (OTs), to give Compound 2.4. Compound 2.4 can react with ammonium to give Compound 1.1 or with a protected ammonium compound, such as NH(t-Boc)$_2$ to give Compound 1.1 after deprotection of the protecting group. Other known methods of converting the acid group (—C(O)OH) to an methyl amino group (—CH$_2$NH$_2$) can also be used.

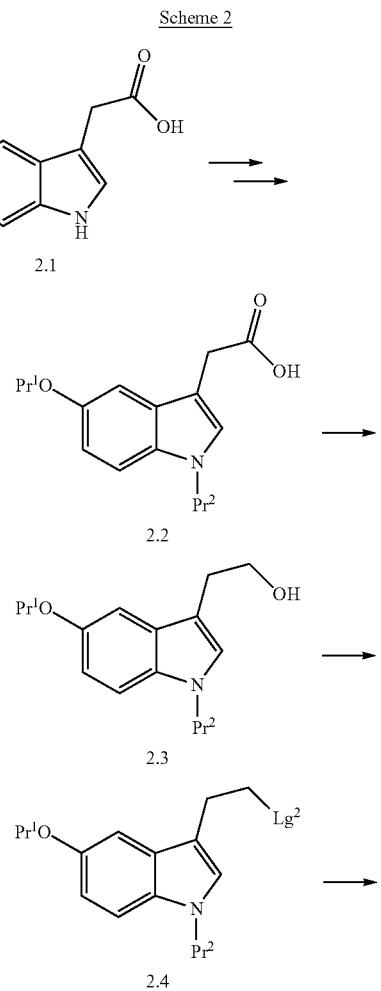

Scheme 2

-continued

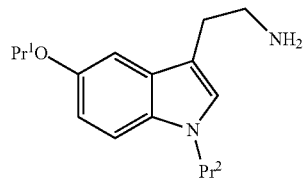

1.1

By using commercially available 5-bromoindole-3-acetic acid and following Scheme 2, the bromo compound corresponding to Compound 1.1 can be prepared, which can be used to replace Compound 1.1 in Scheme 1 to prepare compounds of this invention wherein R is bromo. The bromo atom can be converted to other R groups as defined for Formula I using procedures known in the art. For example, reaction with a suitable agent, such as haloalkyl, haloalkenyl, or haloalkynyl, optionally in the presence of a copper (I) or palladium catalyst and/or a base, such as triethylamine, would give compounds where R is alkyl (when using haloalkenyl or haloalkynyl, the double bond or triple bond can be reduced by hydrogenation).

Scheme 3 shows an example of preparing an intermediate Compound 3.5, which may be used in Scheme 1 to replace Compound 1.1 to prepare compounds of this invention where R is chloro. In Scheme 3, Compound 3.1 (5-chloroindole-3-carboxaldehyde, which is commercially available, for example, from Sigma-Aldrich Corp.) is protected with $Pr^2$ to give Compound 3.2. Compound 3.2 may react with a Wittig agent, e.g. $Ph_3PCH_3^+Br^-$, to give Compound 3.3. Compound 3.3 is converted to Compound 3.4, wherein Halo is a halo such as Br or Cl, by reacting with, for example, hydrogen bromide (HBr). Compound 3.4 can react with ammonium to give Compound 3.5 or with a protected ammonium compound, such as $NH(t-Boc)_2$ to give Compound 3.5 after deprotection of the protecting group. Other known methods of converting the acid group (—C(O)OH) to an methyl amino group (—$CH_2NH_2$) can also be used.

Scheme 3

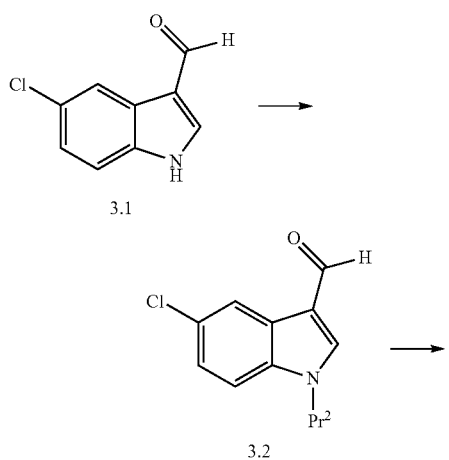

-continued

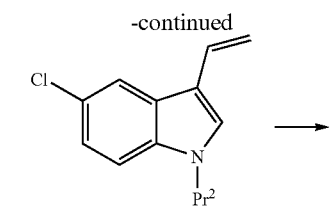

3.3

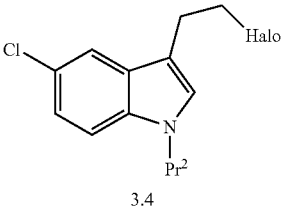

3.4

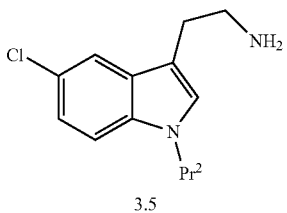

3.5

Further compounds of the present invention can be prepared according to Scheme 4 from noribogaine derivatives (as can be prepared by the synthesis disclosed above, for example) by methods known to one of skill in the art. A skilled artisan would appreciate that the reactivity of the hydroxy group and the indole nitrogen is different so that selectivity can be achieved by selecting suitable reagents and suitable reaction conditions for one of them to react but leaving the other intact to form the desired product. For example, the hydroxy group is expected to selectively react with a carboxylic acid in the presence of triphenylphosphine ($Ph_3P$) and diethyl azodicarboxylate (DEAD) to give Compound 4.1 and Compound 4.3 where L is —C(O)alkylene or —C(O)arylene. Thus, as shown in Scheme 4, noribogaine derivatives can react with appropriately protected compounds of formula LG-$R^{30}$ where $R^{30}$ is -$L^1$-$R^{17}$, -$L^1$-$R^{18}$, -$L^1$-$R^{19}$ or -$L^1$-$CHR^{17}R^{18}$, LG is a leaving group such as hydroxy, alkoxy, halo, etc., to give Compound 4.2, which may further react with LG-$R^{12}$ to form Compound 4.3. In other embodiments (i.e. when $R^{30}$ is H), the C12-phenol, thiol, or amino group is protected by reaction with a suitable protecting group, PG-LG, where LG is a leaving group such as defined above, such that the indole nitrogen is selectively derivatized with $R^{12}$. Suitable protecting groups are well known in the art (see T. W. Greene, P. G. M. Wuts, Protective Groups in Organic Synthesis, $4^{th}$ Edition, Wiley-Interscience, New York, 2006). In another alternative embodiment (i.e. when $R^{12}$ is H), the indole nitrogen is protected with a suitable protecting group, PG (see Greene et al., supra), such that the C12-phenol, thiol, or amino group is free to be derivatized with $R^{30}$.

Scheme 4

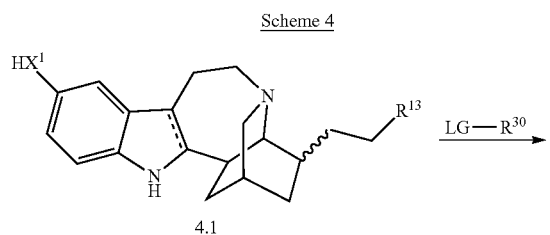
4.1

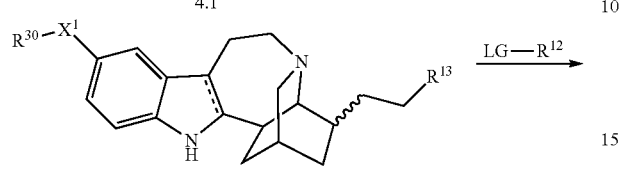
4.2

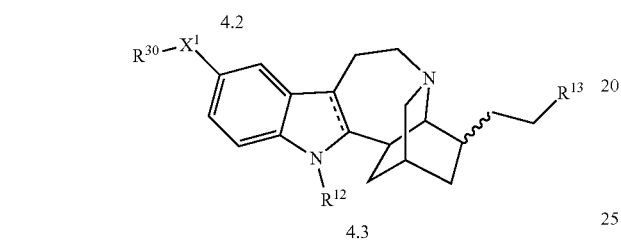
4.3

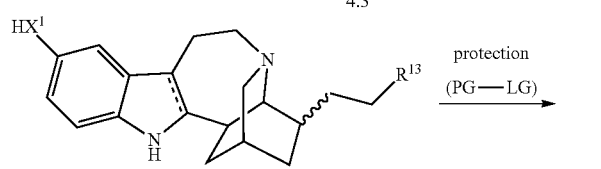

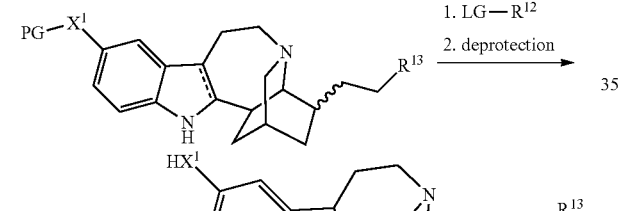

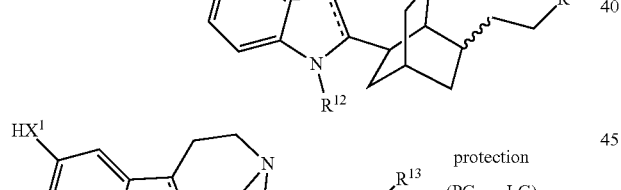

Scheme 5

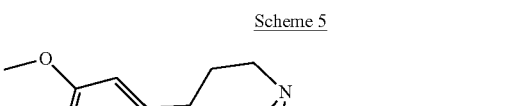
5.1

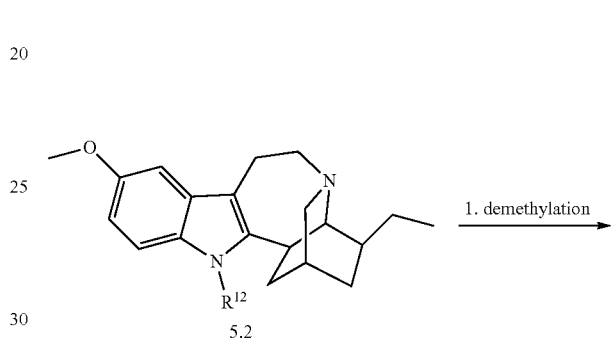
5.2 demethylated by methods known in the art, such as reaction with boron tribromide/methylene chloride at room temperature to give Compound 5.2, which may further react with LG-R$^{30}$ to give Compound 5.3.

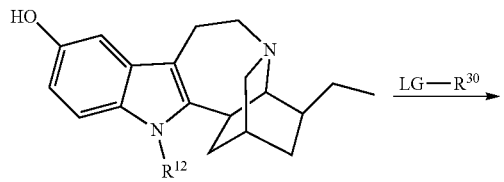
5.3

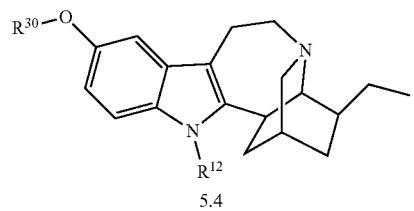
5.4

Alternatively, as shown in Scheme 5, certain compounds of this invention may be prepared by reacting ibogaine with LG-R$^{12}$ to give Compound 5.1. Compound 5.1 can be Compounds of formula IC are prepared from a known starting material, voacangine, as shown in the scheme 6 below.

Scheme 6

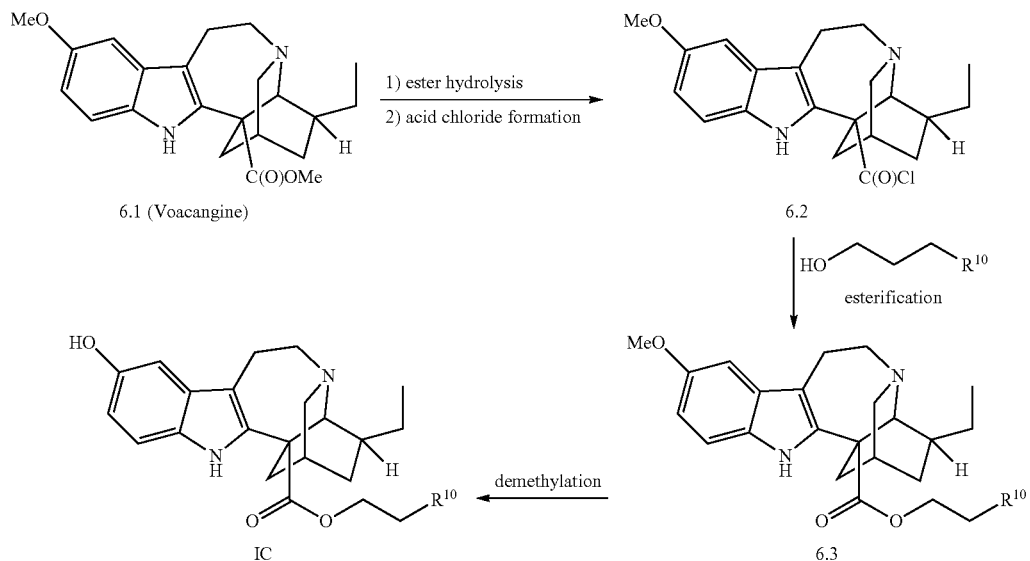

The carboxymethyl group in Voacangine is hydrolyzed or converted into lithium salt using an organolithium reagent such as butyllithium and propanethiol in a solvent such as HMPA/THF. The lithium salt is then converted to the acid chloride 6.2 by reacting with oxalyl chloride in presence of a base such as pyridine in a solvent such as THF. The acid chloride 6.2 is then esterified with an alcohol to give the ester 6.3. Demethylation of the ester with a reagent such as $BBr_3$ in a solvent such as methylene chloride gives compounds of formula IC.

Alternatively, as shown in Schemes 7 and 8, certain compounds of this invention may be prepared using noribogaine, which may be prepared according to known procedures, such as by demethylating ibogaine by methods known in the art, such as reaction with boron tribromide/methylene chloride at room temperature.

Schemes 7 and 8 below show reaction schemes for the sulfation of the 12-hydroxyl group and optionally for the disulfation of the 12-hydroxyl group and the indole nitrogen atom. Scheme 8 below shows reaction schemes for selective sulfation of the indole nitrogen atom by protecting the 12-hydroxyl group with a conventional hydroxyl protecting group. A variety of protecting groups, preferably those stable under acidic conditions are useful as the Pg, as will be apparent to the skilled artisan. An ester of the chlorosulfonic acid may be used to prepare an ester of the compound of Formula I. It is also contemplated that the indole nitrogen of noribogaine can be protected, the sulfation carried out on the hydroxy group of noribogaine, following which, the N-protecting group is deprotected. Methods for preparing the N-protected noribogaine will be apparent to the skilled artisan in view of this disclosure.

Scheme 7

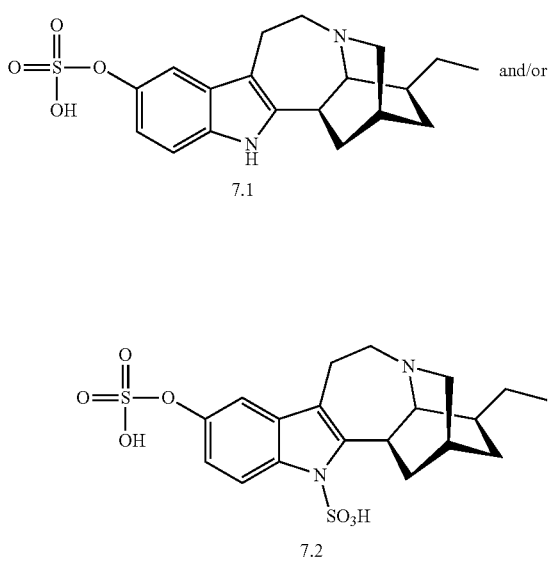

Scheme 8

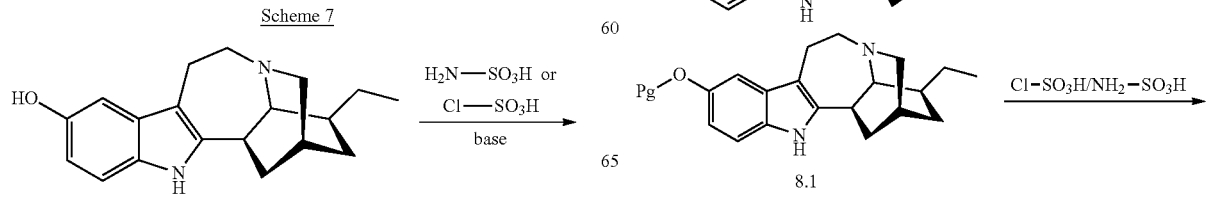

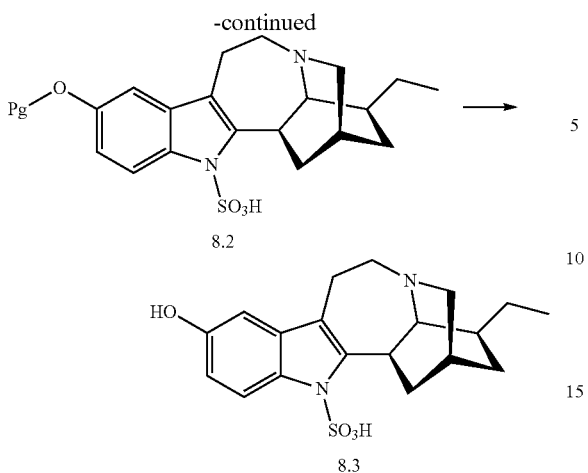

8.2

8.3

As shown above, X refers to a leaving group such a chloro, bromo, iodo, or a $R_s$—$SO_3$-moiety, where $R_s$ is $C_1$-$C_6$ alkyl optionally substituted with 1-3 fluoro atoms or $R_s$ is phenyl optionally substituted with 1-3 halo or $C_1$-$C_6$ alkyl groups.

The dihydronoribogaine compounds of Formula IB are synthesized by reducing the double bond of the corresponding noribogaine derivative. Various reducing agents well known to the skilled artisan are useful for this purpose. For example, catalytic hydrogenation employing hydrogen and a catalyst such as Pd/C or Pt/C is useful for providing the 9,17 cis, i.e. the α,α or the β,β dihydro compounds. Reagents such as borohydride or aluminum hydrides are useful for providing the α,β or the β,α dihydro compounds.

As shown in Schemes 7 and 8, the phosphate derivatives at 12-hydroxy group, indole nitrogen, and both positions are synthesized in an analogous manner via phosphorylation instead of sulfation.

Compounds of this invention as represented by Formula 1-1 can be prepared from noribogaine using an appropriate phosphate source, such as phosphoric acid or a phosphoramidite such as di-tert-butyl N,N-diisopropylphosphoramidite. Compounds of Formula 1-2 can be prepared from compounds of Formula 1-1 using an appropriate phosphate source under known reaction conditions. The reactions are carried out for a period of time sufficient to provide a substantial amount of the product, which can be ascertained by using routine methods such as thin layer chromatography, $^1$H-nuclear magnetic resonance (NMR) spectroscopy, and the likes. Compounds of Formula 1-1 and 1-2 can be isolated and optionally purified using standard purification techniques, such as liquid chromatography. Scheme 2 follows much of the chemistry of Scheme 1 with the exception that a blocking (protecting group—Pg) is used to avoid phosphorylation of the 12 hydroxyl group.

The dihydronoribogaine compounds of Formulas I, I-A, and II are synthesized by reducing the corresponding double bond of noribogaine. Various reducing agents well known to the skilled artisan are useful for this purpose. For example, catalytic hydrogenation employing hydrogen and a catalyst such as Pd/C or Pt/C is useful for providing the 9.17 cis, i.e. the α,α or the β,β dihydro compounds. Reagents such as borohydride or aluminum hydrides are useful for providing the α,β or the β,α dihydro compounds.

It will be apparent to those skilled in the art that many modifications of the above exemplifying methods, both to materials and methods, may be practiced without departing from the scope of the current invention.

What is claimed is:
1. A compound of Formula IA or Formula IB, or a pharmaceutically acceptable salt of each thereof:

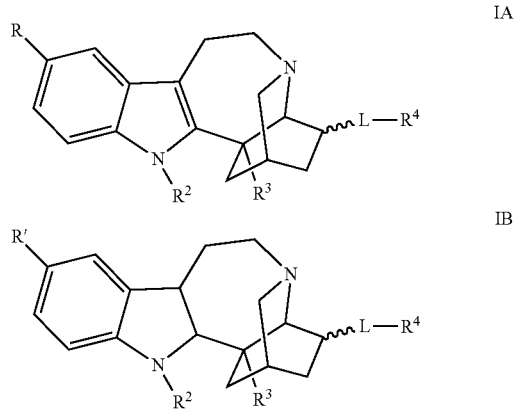

wherein
R is $OR^1$ or $C_1$-$C_{12}$ alkyl optionally substituted with 1 to 5 $R^9$;
$R^1$ is selected from the group consisting of hydrogen, —C(O)OX, —SO$_2$OR$^{10}$, a monophosphate, a diphosphate, a triphosphate, and —C(O)N(Y)$_2$ where X is $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$ heteroaryl having 1 to 4 heteroatoms and which is optionally substituted with 1 to 5 $R^9$, $C_1$-$C_{10}$ heterocyclic having 1 to 4 heteroatoms and which is optionally substituted with 1 to 5 $R^9$, or where each Y, together with the nitrogen atom bound thereto form either a $C_1$-$C_6$ heterocyclic having 1 to 4 heteroatoms and which is optionally substituted with 1 to 5 $R^9$, or a $C_1$-$C_6$ heteroaryl having 1 to 4 heteroatoms and which is optionally substituted with 1 to 5 $R^9$;
R' is halo, $OR^{20}$, or $C_1$-$C_{12}$ alkyl optionally substituted with 1 to 5 $R^9$;
$R^{20}$ is selected from the group consisting of hydrogen, —C(O)X, —C(O)OX and —C(O)N(Y)$_2$ where X and Y are defined as above;
$R^2$ is hydrogen, —SO$_2$OR$^{10}$, a monophosphate, a diphosphate, or a triphosphate;
$R^3$ is selected from the group consisting of hydrogen, —(CH$_2$)$_m$OR$^7$, —CR$^6$(OH)R$^7$, —(CH$_2$)$_m$CN, —(CH$_2$)$_m$ COR$^7$, —(CH$_2$)$_m$CO$_2$R$^7$, —(CH$_2$)$_m$C(O)NR$^6$R$^7$, —(CH$_2$)$_m$C(O)NR$^6$NR$^7$R$^7$, —(CH$_2$)$_m$C(O)NR$^6$NR$^7$C(O)R$^8$, and —(CH$_2$)$_m$NR$^6$R$^7$;
m is 0, 1, or 2;
L is a bond or $C_1$-$C_{12}$ alkylene;
$R^4$ is selected from the group consisting of $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)$_n$—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;
$X^2$ is selected from the group consisting of O and S;
$Y^2$ is $C_1$-$C_4$ alkylene or $C_6$-$C_{10}$ arylene, or a combination thereof;
n is 1, 2, or 3;

$R^6$ and $R^7$ are each independently selected from the group consisting of hydrogen, $C_1$-$C_{12}$ alkyl optionally substituted with 1 to 5 $R^9$, $C_1$-$C_6$ heterocycle having 1 to 4 heteroatoms which is optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$; or $R^6$ and $R^7$ are joined to form $C_1$-$C_6$ heterocycle having 1 to 4 heteroatoms which is optionally substituted with 1 to 5 $R^9$;

$R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^9$ is selected from the group consisting of $C_1$-$C_4$ alkyl, phenyl, halo, —OH, —$OR^{10}$, —CN, —$COR^{10}$, —$CO_2R^{10}$, —$C(O)NHR^{10}$, —$NR^{10}R^{10}$, —$C(O)NR^{10}R^{10}$, —$C(O)NHNHR^{10}$, —$C(O)NR^{10}NHR^{10}$, —$C(O)NR^{10}NR^{10}R^{10}$, —$C(O)NHNR^{10}C(O)R^{10}$, —$C(O)NHNHC(O)R^{10}$, —$SO_2NR^{10}R^{10}$, —$C(O)NR^{10}NR^{10}C(O)R^{10}$, —$NHC(O)R^{10}$, $C_1$-$C_6$ heterocycle having 1 to 4 heteroatoms optionally substituted with 1 to 5 $R^{10}$, and —$C(O)NR^{10}NHC(O)R^{10}$; and $R^{10}$ is $C_1$-$C_{12}$ alkyl;

provided that:

for the compound of Formula IA, when R is —OH or $C_1$-$C_{12}$ alkyl optionally substituted with 1 to 5 $R^9$, then $R^3$ is hydrogen; and for the compound of Formula IA, when $R^3$ is hydrogen, and -L-$R^4$ is ethyl, then R is not —$OR^1$.

2. A compound of Formula IIA or Formula IIB, or a pharmaceutically acceptable salt of each thereof:

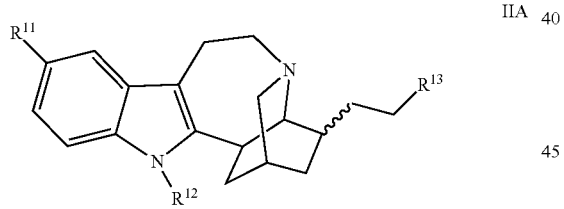

IIA

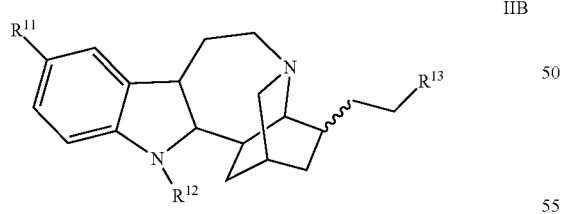

IIB wherein $R^{11}$ is halo, —OH, —SH, —$NH_2$, —$S(O)_2N(R^{16})_2$, —$X^1$-$L^1$-$R^{17}$, —$X^1$-$L^1$-$R^{18}$, —$X^1$-$L^1$-$R^{19}$, or —$X^1$-$L^1$-$CHR^{17}R^{18}$, where $X^1$ is O, S or $NR^{16}$, or —O-Q, where Q is —$SO_2$—($C_1$-$C_{12}$ alkyl), a monophosphate, a diphosphate, or a triphosphate;

$L^1$ is alkylene, arylene, —C(O)-alkylene, —C(O)-arylene, —C(O)O-arylene, —C(O)O— alkylene, —$C(O)NR^{19}$-alkylene, —$C(O)NR^{19}$-arylene, —$C(NR^{19})NR^{19}$-alkylene or —$C(NR^{19})NR^{19}$-arylene, wherein $L^1$ is configured such that —O-$L^1$-$R^{17}$ is —OC(O)-alkylene-$R^{17}$, —OC(O)O-arylene-$R^{17}$, —OC(O)O-alkylene-$R^{17}$, —OC(O)-arylene-$R^{17}$, —OC(O)$NR^{19}$-alkylene-$R^{17}$, —OC(O)$NR^{19}$-arylene-$R^{17}$, —OC($NR^{19}$)$NR^{19}$-alkylene-$R^{17}$ or —OC($NR^{19}$)$NR^{19}$-arylene-$R^{17}$, and wherein the alkylene and arylene are optionally substituted with 1 to 2 $R^{15}$;

$R^{12}$ is hydrogen, —$S(O)_2OR^{19}$, —$S(O)_2R^{19}$, —$C(O)R^{14}$, —$C(O)NR^{14}R^{14}$, —$C(O)OR^{14}$, $C_1$-$C_{12}$ alkyl optionally substituted with 1 to 5 $R^{15}$, $C_1$-$C_{12}$ alkenyl optionally substituted with 1 to 5 $R^{15}$, aryl optionally substituted with 1 to 5 $R^{15}$, —$SO_2$—($C_1$-$C_{12}$ alkyl), a monophosphate, a diphosphate, or a triphosphate;

$R^{13}$ is hydrogen, halo, —$OR^{16}$, —CN, $C_1$-$C_{12}$ alkyl, $C_1$-$C_{12}$ alkoxy, aryl or aryloxy, where the alkyl, alkoxy, aryl, and aryloxy are optionally substituted with 1 to 5 $R^{15}$;

each $R^{14}$ is independently selected from the group consisting of hydrogen, $C_1$-$C_{12}$ alkyl, $C_2$-$C_{12}$ alkenyl, $C_2$-$C_{12}$ alkynyl, aryl, heteroaryl, and heterocycle, and wherein the alkyl, alkenyl, alkynyl, aryl, heteroaryl, and heterocycle are optionally substituted with 1 to 5 $R^{15}$;

$R^{15}$ is selected from the group consisting of phenyl, halo, —$OR^{16}$, —CN, —$COR^{16}$, —$CO_2R^{16}$, —$NR^{16}R^{16}$, —$NR^{16}C(O)R^{16}$, —$NR^{16}SO_2R^{16}$, —$C(O)NR^{16}R^{16}$, —$C(O)NR^{16}NR^{16}R^{16}$, —$SO_2NR^{16}R^{16}$ and —$C(O)NR^{16}NR^{16}C(O)R^{16}$;

each $R^{16}$ is independently hydrogen or $C_1$-$C_{12}$ alkyl optionally substituted with from 1 to 3 halo;

$R^{17}$ is hydrogen, —$C(O)R^{19}$, —$C(O)OR^{19}$, —$C(O)N(R^{19})_2$ or —$N(R^{19})C(O)R^{19}$;

$R^{18}$ is hydrogen, —$N(R^{19})_2$, —$C(O)N(R^{19})_2$, —$C(NR^{19})N(R^{19})_2$, —$C(NSO_2R^{19})N(R^{19})_2$, —$NR^{19}C(O)N(R^{19})_2$, —$NR^{19}C(S)N(R^{19})_2$, —$NR^{19}C(NR^{19})N(R^{19})_2$, —$NR^{19}C(NSO_2R^{19})N(R^{19})_2$ or tetrazole; and each $R^{19}$ is independently selected from the group consisting of hydrogen, $C_1$-$C_{12}$ alkyl and aryl;

provided that:

for the compound of Formula IIA:

when $R^{12}$ and $R^{13}$ are hydrogen, then $R^{11}$ is not hydroxy;

when $R^{13}$ is hydrogen, $R^{11}$ is —O-$L^1$-$R^{17}$, —O-$L^1$-$R^{18}$, —O-$L^1$-$R^{19}$, and $L^1$ is alkylene, then —O-$L^1$-$R^{17}$, —O-$L^1$-$R^{18}$, —O-$L^1$-$R^{19}$ are not methoxy; and when $R^{13}$ is hydrogen, $X^1$ is O, $L^1$ is —C(O)-alkylene, —C(O)-arylene, —C(O)O-arylene, —C(O)O-alkylene, —$C(O)NR^{19}$-alkylene, or —$C(O)NR^{19}$-arylene, then none of $R^{17}$, $R^{18}$ or $R^{19}$ are hydrogen.

3. The compound of claim 2, represented by Formula IIC or Formula IID, or a pharmaceutically acceptable salt of each thereof:

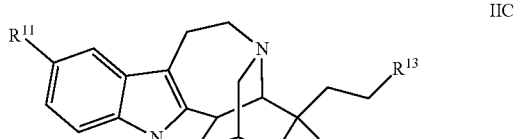

IIC

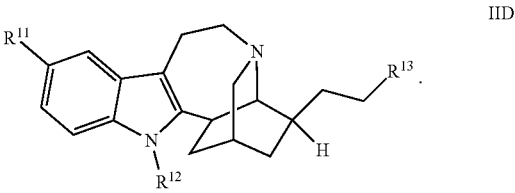

IID

4. The compound of claim 2, wherein $R^{11}$ is halo.

5. The compound of claim 2, wherein $R^{11}$ is bromo.

6. The compound of claim 2, wherein $R^{11}$ is —OH, —O-$L^1$-$R^{17}$, —O-$L^1$-$R^{18}$, —O-$L^1$-$R^{19}$ or —O-$L^1$-$CHR^{17}R^{18}$.

7. The compound of claim 2, wherein $R^{11}$ is —SH, —O-$L^1$-$R^{17}$, —O-$L^1$-$R^{18}$, —O-$L^1$-$R^{19}$ or —S-$L^1$-$CHR^{17}R^{18}$.

8. The compound of claim 2, wherein $R^{11}$ is —$NH_2$, —$NR^{16}$-$L^1$-$R^{17}$, —$NR^{16}$-$L^1$-$R^{18}$, —$NR^{16}$-$L^1$-$R^{19}$ or —$NR^{16}$-$L^1$-$CHR^{17}R^{18}$.

9. The compound of claim 2, wherein $R^{11}$ is —$S(O)_2N(R^{16})_2$.

10. The compound of claim 2, wherein $R^{11}$ is —Cl, —Br, —I, —OC(O)$CH_2CH_3$, —OC(O)$CH_2$Ph, —OC(O)O$CH_2CH_3$, —OC(O)O$CH_2$Ph, —OC(O)NH(CH($CH_3$)Ph), —OC(NPh)NH$CH_2CH_3$, —OC(O)NH$CH_2$Ph, —$NH_2$, —NHC(O)C($CH_3$)$_3$, —NHC(O)$CF_3$, —NHC(O)$CH_2$Ph, —NHC(O)O$CH_2$Ph, —NHC(O)NH(CH($CH_3$)Ph), —SH, —SC(O)O$CH_2$Ph, —SC(O)NH(CH($CH_3$)Ph), —OC(O)$CH_2CH_2$CH($NH_2$)($CO_2H$), or —NHC(O)$CH_2CH_2$CH($NH_2$)($CO_2H$).

11. The compound of claim 2, wherein $R^{12}$ is hydrogen.

12. The compound of claim 2, wherein $R^{12}$ is —$CH_2CH_3$, —$CH_2$CHCH$_2$, —$CH_2$Ph, —C(O)O($CH_2$)$_2$N($CH_3$)$_2$ or —C(O)$CH_2$($CH_2$)$_2$$SO_2$N($CH_3$)$_2$.

13. The compound of claim 2, wherein $R^{13}$ is hydrogen.

14. The compound of claim 2, wherein $R^{13}$ is alkyl substituted with from 1 to 3 halo.

15. The compound of claim 2, wherein $R^{13}$ is trifluoromethyl.

16. The compound of claim 2, wherein $R^{13}$ is —$OCH_3$, —$OCH_2CH_3$, —$OCH_2$Ph or —CN.

17. A compound of Formula IIE or a pharmaceutically acceptable salt thereof:

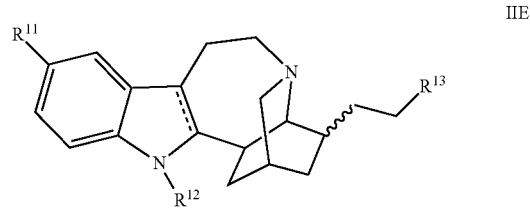

IIE wherein the compound is selected form the group consisting of compounds wherein $R^{11}$, $R^{12}$, $R^{13}$ are defined as follows:

| No. | $R^{11}$ | $R^{12}$ | $R^{13}$ | ===== |
|---|---|---|---|---|
| 1 | Cl | H | H | double bond |
| 2 | Br | H | H | double bond |
| 3 | I | H | H | double bond |
| 5 | —OC(O)$CH_2$Ph | H | H | double bond |
| 6 | —OC(O)O$CH_2CH_3$ | H | H | double bond |
| 7 | —OC(O)O$CH_2$Ph | H | H | double bond |
| 8 | —OC(O)NH(CH($CH_3$)Ph) | H | H | double bond |
| 9 | —OC(NPh)NH$CH_2CH_3$ | H | H | double bond |
| 10 | —OC(O)NH$CH_2$Ph | H | H | double bond |
| 11 | —$NH_2$ | H | H | double bond |
| 12 | —NHC(O)C($CH_3$)$_3$ | H | H | double bond |
| 13 | —NHC(O)$CF_3$ | H | H | double bond |
| 14 | —NHC(O)$CH_2$Ph | H | H | double bond |
| 15 | —NHC(O)O$CH_2$Ph | H | H | double bond |
| 16 | —NHC(O)NH(CH($CH_3$)Ph) | H | H | double bond |
| 17 | —SH | H | H | double bond |
| 18 | —SC(O)O$CH_2$Ph | H | H | double bond |
| 19 | —SC(O)NH(CH($CH_3$)Ph) | H | H | double bond |
| 20 | —SC(O)$CH_2CH_2$OP(O)(OH)$_2$ | H | H | double bond |
| 21 | —OC(O)$CH_2CH_2$CH($NH_2$)($CO_2H$) | H | H | double bond |
| 22 | —O—(2-OH—$C_6H_3$)$CH_2$CH($NH_2$)($CO_2H$) | H | H | double bond |
| 23 | —NHC(O)$CH_2CH_2$CH($NH_2$)($CO_2H$) | H | H | double bond |
| 24 | —OH | H | H | single bond |
| 25 | Cl | H | H | single bond |
| 26 | Br | H | H | single bond |

-continued

| No. | R¹¹ | R¹² | R¹³ | ===== |
|-----|-----|-----|-----|-------|
| 27 | I | H | H | single bond |
| 28 | —OC(O)CH₂CH₃ | H | H | single bond |
| 29 | —OC(O)OCH₂Ph | H | H | single bond |
| 30 | —OC(O)NH(CH(CH₃)Ph) | H | H | single bond |
| 31 | —OC(O)NHCH₂Ph | H | H | single bond |
| 32 | —NH₂ | H | H | single bond |
| 33 | —NHC(O)C(CH₃)₃ | H | H | single bond |
| 34 | —NHC(O)NH(CH(CH₃)Ph) | H | H | single bond |
| 35 | —SH | H | H | single bond |
| 36 | —SC(O)OCH₂Ph | H | H | single bond |
| 37 | —OH | —CH₂CH₃ | H | double bond |
| 38 | —OH | —CH₂CHCH₂ | H | double bond |
| 39 | —OH | —CH₂Ph | H | double bond |
| 40 | —OH | —C(O)O(CH₂)₂N(CH₃)₂ | H | double bond |
| 41 | —OH | —C(O)CH₂(CH₂)₂SO₂N(CH₃)₂ | H | double bond |
| 42 | —OH | H | —OCH₂CH₃ | double bond |
| 43 | —OH | H | —OCH₂Ph | double bond |
| 44 | —OH | H | —CF₃ | double bond |
| 45 | —OH | H | —OH | double bond |
| 46 | —OH | H | —CN | double bond. |

18. A compound of formula IC:

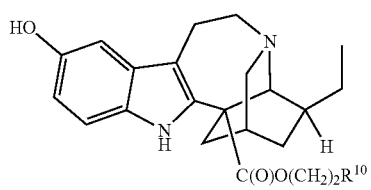

1C or a pharmaceutically acceptable salt thereof, wherein the compound is selected form the group consisting of compounds wherein R¹⁰ is defined as follows:

TABLE 2

| No. | R¹⁰ |
|-----|-----|
| 47 | NMe₂ |
| 48 | OH |
| 49 | NHC(O)Me |
| 50 | OMe |
| 51 | ⌐N⌐ (azetidinyl) |

TABLE 2-continued

| No. | R¹⁰ |
|-----|-----|
| 52 | pyrrolidinyl |
| 53 | Me—N(piperazinyl)N— |
| 54 | morpholinyl |

19. A composition comprising a compound of claim 1 or 2 and a pharmaceutically acceptable excipient.

20. A method of treating pain in a patient, comprising administering to said patient: a compound of claim 1 or 2 or a pharmaceutically acceptable salt thereof.

21. The method of claim 20, which method is for treating neuropathic pain.

22. The method of claim 20, which method is for treating nociceptive pain.

23. A method of treating pain in a patient, comprising administering to said patient a composition of claim 19.

* * * * *